United States Patent
Govindan et al.

(10) Patent No.: US 8,338,140 B2
(45) Date of Patent: Dec. 25, 2012

(54) POLYMERIC CARRIERS OF THERAPEUTIC AGENTS AND RECOGNITION MOIETIES FOR ANTIBODY-BASED TARGETING OF DISEASE SITES

(75) Inventors: Serengulam V. Govindan, Summit, NJ (US); Sung-Ju Moon, New Providence, NJ (US); David M. Goldenberg, Mendham, NJ (US); Chien-Hsing Chang, Downingtown, PA (US)

(73) Assignee: Immunomedics, Inc., Morris Plains, NJ (US)

(*) Notice: Subject to any disclaimer, the term of this patent is extended or adjusted under 35 U.S.C. 154(b) by 0 days.

(21) Appl. No.: 13/246,389

(22) Filed: Sep. 27, 2011

(65) Prior Publication Data
US 2012/0040431 A1    Feb. 16, 2012

Related U.S. Application Data

(60) Division of application No. 12/766,092, filed on Apr. 23, 2010, now Pat. No. 8,067,006, which is a continuation-in-part of application No. 11/961,436, filed on Dec. 20, 2007, now abandoned, and a continuation-in-part of application No. 12/731,781, filed on Mar. 25, 2010, now Pat. No. 8,003,111, and a continuation-in-part of application No. 12/644,146, filed on Dec. 22, 2009, now Pat. No. 7,981,398, which is a division of application No. 11/925,408, filed on Oct. 26, 2007, now Pat. No. 7,666,400, said application No. 12/766,092 is a continuation-in-part of application No. 12/417,917, filed on Apr. 3, 2009, now Pat. No. 7,906,121, which is a division of application No. 11/478,021, filed on Jun. 29, 2006, now Pat. No. 7,534,866, said application No. 12/766,092 is a continuation-in-part of application No. 12/396,965, filed on Mar. 3, 2009, now Pat. No. 7,871,622, which is a division of application No. 11/391,584, filed on Mar. 28, 2006, now Pat. No. 7,521,056, said application No. 12/766,092 is a continuation-in-part of application No. 12/396,605, filed on Mar. 3, 2009, now Pat. No. 7,858,070, which is a division of application No. 11/633,729, filed on Dec. 5, 2006, now Pat. No. 7,527,787, which is a continuation-in-part of application No. PCT/US2006/010762, filed on Mar. 24, 2006, and a continuation-in-part of application No. PCT/US2006/012084, filed on Mar. 29, 2006, and a continuation-in-part of application No. PCT/US2006/025499, filed on Jun. 29, 2006, and a continuation-in-part of application No. 11/389,358, filed on Mar. 24, 2006, now Pat. No. 7,550,143, said application No. 12/766,092 is a continuation-in-part of application No. 12/418,877, filed on Apr. 6, 2009, now Pat. No. 7,906,118.

(60) Provisional application No. 60/885,325, filed on Jan. 17, 2007, provisional application No. 61/163,666, filed on Mar. 26, 2009, provisional application No. 60/864,530, filed on Nov. 6, 2006, provisional application No. 60/668,603, filed on Apr. 6, 2005, provisional application No. 61/043,932, filed on Apr. 10, 2008, provisional application No. 61/104,916, filed on Oct. 13, 2008, provisional application No. 61/119,542, filed on Dec. 3, 2008, provisional application No. 60/728,292, filed on Oct. 19, 2005, provisional application No. 60/751,196, filed on Dec. 16, 2005, provisional application No. 60/782,332, filed on Mar. 14, 2006.

(51) Int. Cl.
| | |
|---|---|
| C07D 491/22 | (2006.01) |
| C07G 11/00 | (2006.01) |
| C07K 16/00 | (2006.01) |
| C07K 9/00 | (2006.01) |
| C08B 37/02 | (2006.01) |
| C08B 37/16 | (2006.01) |

(52) U.S. Cl. ............... 435/103; 530/322; 530/391.7; 536/112; 536/16.8; 546/48; 436/529; 514/59; 514/68; 514/150; 514/11.1; 514/221; 514/237.2; 977/754; 977/729; 977/918

(58) Field of Classification Search ................... None
See application file for complete search history.

(56) References Cited

U.S. PATENT DOCUMENTS
4,046,722 A    9/1977 Rowland
(Continued)

FOREIGN PATENT DOCUMENTS
WO    00/68248    11/2000
(Continued)

OTHER PUBLICATIONS
Moon et al, J Med Chem 51: 6916-6926, Nov. 2008.*
(Continued)

*Primary Examiner* — Phuong Huynh
(74) *Attorney, Agent, or Firm* — Richard A. Nakashima

(57) ABSTRACT

The present invention concerns methods and compositions for delivery of therapeutic agents to target cells, tissues or organisms. In preferred embodiments, the therapeutic agents are delivered in the form of therapeutic-loaded polymers that may comprise many copies of one or more therapeutic agents. In more preferred embodiments, the polymer may be conjugated to a peptide moiety that contains one or more haptens, such as HSG. The agent-polymer-peptide complex may be delivered to target cells by, for example, a pre-targeting technique utilizing bispecific or multispecific antibodies or fragments, having at least one binding arm that recognizes the hapten and at least a second binding arm that binds specifically to a disease or pathogen associated antigen, such as a tumor associated antigen. Methods for synthesizing and using such therapeutic-loaded polymers and their conjugates are provided.

15 Claims, No Drawings

U.S. PATENT DOCUMENTS

| | | | |
|---|---|---|---|
| 4,699,784 | A | 10/1987 | Shih et al. |
| 4,868,109 | A | 9/1989 | Lansdorp et al. |
| 5,635,603 | A | 6/1997 | Hansen et al. |
| 5,770,198 | A | 6/1998 | Coller et al. |
| 6,261,537 | B1 | 7/2001 | Klaveness et al. |
| 6,306,393 | B1 | 10/2001 | Goldenberg |
| 6,468,530 | B1 | 10/2002 | Goldenberg et al. |
| 6,524,854 | B1 | 2/2003 | Monia et al. |
| 6,831,158 | B2 | 12/2004 | Nissen et al. |
| 7,060,506 | B2 | 6/2006 | Craig |
| 7,067,128 | B2 | 6/2006 | Goldenberg et al. |
| 7,151,164 | B2 | 12/2006 | Hansen et al. |
| 7,230,068 | B2 | 6/2007 | Wilson |
| 7,521,056 | B2 | 4/2009 | Chang et al. |
| 7,527,787 | B2 | 5/2009 | Chang et al. |
| 7,534,866 | B2 | 5/2009 | Chang et al. |
| 7,541,440 | B2 | 6/2009 | Goldenberg et al. |
| 7,550,143 | B2 | 6/2009 | Chang et al. |
| 7,591,994 | B2 | 9/2009 | Govindan et al. |
| 7,642,239 | B2 | 1/2010 | Taylor et al. |
| 7,666,400 | B2 | 2/2010 | Chang et al. |
| 7,871,622 | B2 | 1/2011 | Chang et al. |
| 7,901,680 | B2 | 3/2011 | Chang et al. |
| 7,906,118 | B2 | 3/2011 | Chang et al. |
| 7,906,121 | B2 | 3/2011 | Chang et al. |
| 7,932,212 | B2 | 4/2011 | Taylor et al. |
| 7,981,398 | B2 | 7/2011 | Chang et al. |
| 2003/0026764 | A1* | 2/2003 | Griffiths ................. 424/9.34 |
| 2003/0198956 | A1 | 10/2003 | Makowski et al. |
| 2003/0232420 | A1 | 12/2003 | Braun et al. |
| 2004/0018587 | A1 | 1/2004 | Makowski et al. |
| 2004/0126361 | A1 | 7/2004 | Saifer et al. |
| 2005/0002945 | A1 | 1/2005 | McBride et al. |
| 2005/0003403 | A1 | 1/2005 | Rossi et al. |
| 2006/0210475 | A1 | 9/2006 | Goldenberg et al. |
| 2007/0264265 | A1 | 11/2007 | Goldenberg et al. |
| 2008/0221300 | A1* | 9/2008 | Tomalia et al. .............. 528/373 |
| 2009/0060862 | A1 | 3/2009 | Chang et al. |
| 2009/0111143 | A1 | 4/2009 | Goldenberg et al. |

FOREIGN PATENT DOCUMENTS

| | | |
|---|---|---|
| WO | 2006/107617 | 10/2006 |
| WO | 2006/107786 | 10/2006 |
| WO | 2007/075270 | 7/2007 |

OTHER PUBLICATIONS

Matarrese et al., "Type I Interferon Gene Transfer Sensitizes Melanoma Cells to Apoptosis via a Target Activity on Mitochondrial Function", Am. J. Pathol. 2002, 160(4):1507-1520.

Mecchia et al., "Type I consensus interferon (CIFN) gene transfer into human melanoma cells up-regulates p53 and enhances cisplatin-induced apoptosis: implications for new therapeutic strategies with IFN-alpha", Gene Ther. (2000) 7, 167-179.

Newlon et al., "A Novel Mechanism of PKA Anchoring Revealed by Solution Structures of Anchoring Complexes", EMBO J. 2001; 20:1651-1662.

Newlon et al., "The molecular basis for protein kinase A anchoring revealed by solution NMR", Nature Struct. Biol. 1999; 3:222-227.

Ngo et al., "Computational Complexity, Protein Structure Prediction, and the Levinthal Paradox", The Protein Folding Problem and Tertiary Structure Prediction, Ch. 14, pp. 492-495, (Mertz & Le Grand, Eds.), Birkhauser Boston, 1994.

Osborn et al., "Pharmacokinetic and Pharmacodynamic Studies of a Human Serum Albumin-Interferon-α Fusion Protein in Cynomolgus Monkeys", J. Pharmacol. Exp. Ther. 303(2):540-548 (2002).

Oyen et al., "Human testis cDNA for the regulatory subunit RIIα of cAMP-dependent protein kinase encodes an alternate amino-terminal region", FEBS Letters 246:57-64, 1989.

Ozzello et al., "Conjugation of interferon alpha to a humanized monoclonal antibody (HuBrE-3vl) enhances the selective localization and antitumor effects of interferon in breast cancer xenografts", Breast Cancer Res. Treat. 48: 135-147 (1998).

Paquette et al., "Interferon-α and granulocyte-macrophage colony-stimulating factor differentiate peripheral blood monocytes into potent antigen-presenting cells", J. Leukoc. Biol. 64:358-367; 1998.

Pelham et al., "Interferon-α conjugation to human osteogenic sarcoma monoclonal antibody 791T/36", Cancer Immunol. Immuother. 1983;15(3):210-216.

Pepinsky et al., "Improved Pharmacokinetic Properties of a Polyethylene Glycol-Modified Form of Interferon-β-1a with Preserved in Vitro Bioactivity", Pharmacol. Exp. Ther. 2001; 297(3):1059-1066.

Pilling et al., "Interferon-β mediates stromal cell rescue of T cells from apoptosis", Eur. J. Immunol. 29:1041-1050 (1999).

Rabjohn et al., "Molecular Cloning and Epitope Analysis of the Peanut Allergen Ara h 3", J. Clinical Investigation 103 (4):535-542 (1999).

Raefsky et al., "Studies of Interferon as a regulator of hematopoietic cells proliferation", J. Immunol. 135 (4):2507-2512 (1985).

Rose et al., "Structural basis of dimerization, coactivator recognition and MODY3 mutations in HNF-1α", Nature Struct. Biol. 2000; 7:744-748.

Rosendahl et al., "A Long-Acting, Highly Potent Interferon α-2 Conjugate Created Using Site-Specific PEGylation", Bioconjugate Chem. 2005;16:200-207.

Rossi et al., "Novel Designs of Multivalent Anti-CD20 Humanized Antibodies as Improved Lymphoma Therapeutics", Cancer Res. 68:8384-92, 2008.

Rossi et al., "Stably tethered multifunctional structures of defined composition made by the dock and lock method for use in cancer targeting", Proc. Natl. Acad. Sci. Epub Apr. 24, 2006, vol. 103, No. 18, pp. 6841-6846.

Rustandi et al., "The Ca2+-Dependent Interaction of S100B(ββ) with a Peptide Derived from p53", Biochemistry 1998; 37: 1951-1960.

Sabaawy et al., "Enhancement of 5-fluorouracil cytotoxicity on human colon cancer cells by retrovirus-mediated interferon-α gene transfer", Int. J. Oncol. Jun. 1999; 14(6):1143-51.

Salles et al., "Rituximab combined with chemotherapy and interferon in follicular lymphoma patients: results of the GELA-GOELAMS FL2000 study", Blood 2008; 112:4824-4831.

Santini et al., "Type I Interferon as a Powerful Adjuvant for Monocyte-derived Dendritic Cell Development and Activity In Vivo and in Hu-PBL-SCID Mice", J. Exp. Med. 191(10):1777-1788 (2000).

Scott et al., "Type II Regulatory Subunit Dimerization Determines the Subcellular Localization of the cAMP-dependent Protein Kinase", J. Biol. Chem. 265:21561-66 (1990).

Scott et al., "Cyclic nucleotide-dependent protein kinases", Pharmacol. Ther. 1991;50(1):123-45.

Seffernick et al., "Melamine Deaminase and Atrazine Chlorohydrolase: 98 Percent Identical but Functionally Different", J. Bacteriol. 183(8):2405-2410 (2001).

Sharkey et al., "Targeted Therapy of Cancer: New Prospects for Antibodies and Immunoconjugates", CA Cancer J. Clin. 56:226-243 (2006).

Sharkey et al., "Improved Therapeutic Results by Pretargeted Radioimmunotherapy of Non-Hodgkin's Lymphoma with a New Recombinant, Trivalent, Anti-CD20, Bispecific Antibody", Cancer Res. 68:5282-90, 2008.

Sharkey et al., "Metastatic Human Colonic Carcinoma: Molecular Imaging with Pretargeted SPECT and PET in a Mouse Model", Radiology 246:497-507, 2008.

Sidky et al., "Inhibition of Angiogenesis by Interferons: Effects on Tumor- and Lymphocyte-induced Vascular Responses", Cancer Res. 47:5155-5161, Oct. 1, 1987.

Stein et al., "Characterization of a New Humanized Anti-CD20 Monoclonal Antibody, IMMU-106, and Its Use in Combination with the Humanized Anti-CD22 Antibody, Epratuzumab, for the Therapy of Non-Hodgkin's Lymphoma", Clin. Cancer Res. vol. 10, 2868-2878, Apr. 15, 2004.

Stein et al., "Characterization of a humanized IgG4 anti-HLA-DR monoclonal antibody that lacks effector cell functions but retains direct antilymphoma activity and increases the potency of rituximab", Blood 2006;108:2736-2744.

Stokka et al., "Characterization of A-kinase-anchoring disruption using a solution-based assay", Biochem. J. (2006) 400, 493-499.

Stryer et al., "Levels of Structure in Protein Architecture", Biochemistry, 3rd Ed., pp. 31-33, W.H. Freeman & Co., New York, 1988.

Takaoka et al., "Integration of interferon-α/β signalling to p53 responses in tumour suppression and antiviral defence", Nature Jul. 31, 2003;424(6948):516-23.

Taylor, S., "cAMP-dependent Protein Kinase", J. Biol. Chem. 1989;264(15):8443-8446.

Uekama et al., "Cyclodextrin Drug Carrier Systems", Chem. Rev. 98(5):2045-2076 (1998).

Walsh et al., "An Adenosine 3', 5'-Monophosphate-dependant Protein Kinase from Rabbit Skeletal Muscle", J. Biol. Chem. 243(13):3763-3774 (1968).

Weck et al., "Comparison of the Antiviral Activities of Various Cloned Human Interferon-α Subtypes in Mammalian Cell Cultures" J. Gen. Virol. (1981), 57, 233-237.

Winkler et al., "Changing the Antigen Binding Specificity by Single Point Mutations of an Anti-p24 (HIV-1) Antibody", J. Immunol. 165:4505-14, 2000.

Witkowski et al., "Conversion of a β-Ketoacyl Synthase to a Malonyl Decarboxylase by Replacement of the Active-Site Cysteine with Glutamine", Biochemistry 38(36):11643-50 (1999).

Wong et al., "AKAP Signalling Complexes: Focal Points in Space and Time", Nat. Rev. Mol. Cell Biol. 12:959-70 (2004).

Zhu et al., "Inhibition of tumor growth and metastasis by targeting tumor-associated angiogenesis with antagonists to the receptors of vascular endothelial growth factor", Invest. New Drugs 17:195-212, 1999.

Li et al., "Cell cycle-dependent migration of the DNA-binding protein Ku80 into nucleoli", Exp Cell Res. Apr. 1992;199 (2):262-8.

Abbas et al., Cellular and Molecular Immunology, W.B. Saunders Comp. 1991, p. 43.

Alto et al., "Bioinformatic design of A-kinase anchoring protein-in silico: a potent and selective peptide antagonist of type II protein kinase A anchoring", Proc. Natl. Acad. Sci USA Apr. 15, 2003; 100(8):4445-50.

Backer et al., "Self-Assembled "Dock and Lock" System for Linking Payloads to Targeting Proteins", Bioconjugate Chem. 17(4):912-919 (2006).

Baillie et al., "Compartmentalisation of phospodiesterases and protein kinase A: opposites attract", FEBS Letters 2005; 579:3264-3270.

Banky et al., "Dimerization/Docking Domain of the Type Iα Regulatory Subunit of cAMP-dependent Protein Kinase", J. Biol. Chem. 273:35048-55, 1998.

Basu et al., "Structure-Function Engineering of Interferon-β-1b for Improving Stability, Solubility, Potency, Immunogenicity, and Pharmacokinetic Properties by Site-Selective Mono-PEGylation", Bioconjugate Chem. 2006; 17:618-630.

Belardelli et al., "Interferon-alpha in tumor immunity and immunotherapy" Cytokine Growth Factor Rev. 13(2):119-134 (2002).

Belardelli et al., "International Meeting on Cancer Vaccines: How Can We Enhance Efficacy of Therapeutic Vaccines?" Cancer Res. 64:6827-6830 (2004).

Belardelli and Gresser, "The neglected role of type I interferon in the T-cell response: implications for its clinical use", Immunol. Today 17(8):369-72 (1996).

Biron et al., "Natural killer cells in antiviral defense: function and regulation by innate cytokines", Annu. Rev. Immunol. 17:189-220 (1999).

Brunda et al., "Modulation of Murine Natural Killer Cell Activity in Vitro and in Vivo by Recombinant Human Interferons", Cancer Res. 44:597-601 (1984).

Burns-Hamuro et al., "Distinct interaction modes of an AKAP bound to two regulatory subunit isoforms of protein kinase A revealed by amide hydrogen/deuterium exchange", Protein Science (2005), 14:2982-2992.

Carr et al., "Interaction of the Regulatory Subunit (RII) of cAMP-dependent Protein Kinase with RII-anchoring Proteins Occurs through an Amphipathic Helix Binding Motif", J. Biol. Chem. 266:14188-92 (1991).

Carr et al., "Identification of Sperm-specific Proteins That Interact with A-kinase Anchoring Proteins in a Manner Similar to the Type II Regulatory Subunit of PKA", J. Biol. Chem. 276(20):17332-17338 (2001).

Carrero et al., "Lymphocytes are detrimental during the early innate immune response against Listeria monocytogenes", J. Exp. Med. 203(4):933-940 (2006).

Chang et al., "The Dock and Lock Method: A Novel Platform Technology for Building Multivalent, Multifunctional Structures of Defined Composition with Retained Bioactivity", Clin. Cancer Res. Sep. 15, 2007;13(18 Suppl), pp. 5586-5591.

Chmura et al., "Antibodies with infinite affinity", Proc. Natl. Acad. Sci. USA 98(15):8480-8484 (2001).

Colledge et al., "AKAPs: from structure to function", Trends Cell Biol. 6:216-21 (1999).

Corbin et al., "Regulation of Adenosine 3',5'-Monophosphate-dependent Protein Kinase", J. Biol. Chem. 248:1813-21 (1973).

Dhalluin et al., "Structural and Biophysical Characterization of the 40 kDa PEG-Interferon-α2a and Its Individual Positional Isomers", Bioconjugate Chem. 2005;16:504-517.

Dodart et al., "Immunotherapy for Alzheimer's Disease: will vaccination work?", Trends Mol. Med. 9(3):85-87 (2003).

Doherty et al., "Site-Specific PEGylation of Engineered Cysteine Analogues of Recombinant Human Granulocyte-Macrophage Colony-Stimulating Factor", Bioconjugate Chem. 2005;16:1291-1298.

Ferrantini et al., "IFN-α1 Gene Expression into a Metastatic Murine Adenocarcinoma (TS/A) Results in CD8+ T Cell-Mediated Tumor Rejection and Development of Antitumor Immunity", J. Immunol. 153:4604-15 (1994).

Ferrantini et al., "Interferon-α and cancer: Mechanisms of action and new perspectives of clinical use", Biochimie 89: 884-893 (2007).

Gillies et al., "High-level expression of chimeric antibodies using adapted cDNA variable region cassettes", J. Immunol. Methods 125 (1989) 191-202.

Glennie et al., "Mechanisms of killing by anti-CD20 monoclonal antibodies", Mol. Immunol. 44:3823-3837 (2007).

Gold et al., "A Novel Bispecific, Trivalent Antibody Construct for Targeting Pancreatic Carcinoma", Cancer Res. 68:4819-26, 2008.

Gold et al., "Molecular Basis of AKAP Specificity for PKA Regulatory Subunits", Mol. Cell Nov. 3, 2006;24(3):383-95.

Goldenberg et al., "Multifunctional Antibodies by the Dock-and-Lock Method for Improved Cancer Imaging and Therapy by Pretargeting", J. Nucl. Med. 49:158-63, 2008.

Goldenberg et al., "Properties and structure-function relationships of veltuzumab (hA20), a humanized anti-CD20 monoclonal antibody", Blood 113:1062-70 (2009).

Goodson et al., "Site-Directed PEGylation of Recombinant Interleukin-2 at its Glycosylation Site", Nat. Biotechnology Apr. 1990;8(4):343-6.

Grace et al., "Site of Pegylation and Polyethylene Glycol Molecule Size Attenuate Interferon-α Antiviral and Antiproliferative Activities through the JAK/STAT Signaling Pathway", J. Biol. Chem. 2005;280(8):6327-6336.

Grimley et al., "Prolonged STAT1 Activation Related to the Growth Arrest of Malignant Lymphoma Cells by Interferon-α", Blood 91(8):3017-27 (1998).

Gutterman et al., "Leukocyte Interferon-Induced Tumor Regression in Human Metastatic Breast Cancer, Multiple Myeloma, and Malignant Lymphoma", Ann. Intern. Med. 93(3):399-406 (1980).

Gutterman et al., "Cytokine therapeutics: Lessons from interferon α", Proc. Natl. Acad. Sci. USA 91:1198-205 (1994).

Harris et al., "Effect of pegylation on pharmaceuticals", Nat. Rev. Drug. Discov. 2:214-221 (2003).

Hausken et al., "Mutational Analysis of the A-Kinase Anchoring Protein (AKAP)-binding Site on RII", J. Biol. Chem. 271:29016-22 (1996).

Hodneland et al., "Selective immobilization of proteins to self-assembled monolayers presenting active site-directed capture ligands", Proc. Natl. Acd. Sci. USA 2002; 99:5048-5052.

Huang et al., "Targeting IFN-α to B Cell Lymphoma by a Tumor-Specific Antibody Elicits Potent Antitumor Activities", J. Immunol. 179:6881-88 (2007).

Hundsrucker et al., "High-affinity AKAP7δ-protein kinase A interaction yields novel protein kinase A-anchoring disruptor peptides", Biochem. J. (2006) 396, 297-306.

Kimby et al., "Long-term molecular remissions in patients with indolent lymphoma treated with rituximab as a single agent or in combination with interferon alpha-2a: A randomized phase II study from the Nordic Lymphoma Group", Leuk. Lymphoma 49(1):102-112 (2008).

Kinderman et al., "A Dynamic Mechanism for AKAP Binding to RII Isoforms of cAMP-Dependent Protein Kinase", Mol. Cell 24(3):397-408 (2006).

Kinstler et al., "Characterization and Stability of N-terminally PEGylated rhG-CSF", Pharm. Res. 1996;13(7):996-1002.

Kolb et al., "The growing impact of click chemistry on drug discovery", Drug Discov. Today, 8(24):1128-37 (2003).

Kramer et al., "Cell and virus sensitivity studies with recombinant human alpha interferons", J. Interferon. Res. 3(4):425-35 (1983).

Le Bon et al., "Type I Interferons Potently Enhance Humoral Immunity and Can Promote Isotype Switching by Stimulating Dendritic Cells In Vivo" Immunity 14:461-470 (2001).

Lee et al., "Solid-Phase PEGylation of Recombinant Interferon α-2a for Site-Specific Modification: Process Performance, Characterization, and in Vitro Bioactivity", Bioconjugate Chem. 2007; 18:1728-34.

Lohmann et al., "High-affinity binding of the regulatory subunit (RII) of cAMP-dependent protein kinase to microtubule-associated and other cellular proteins", Proc. Natl. Acad. Sci. USA 81:6723-27 (1984).

Luft et al., "Type I IFNs Enhance the Terminal Differentiation of Dendritic Cells", J. Immunol. 161:1947-1953 (1998).

Mason, Anthony J., "Functional Analysis of the Cysteine Residues of Activin A", Mol. Endocrinol. 8:325-32, 1994.

* cited by examiner

POLYMERIC CARRIERS OF THERAPEUTIC AGENTS AND RECOGNITION MOIETIES FOR ANTIBODY-BASED TARGETING OF DISEASE SITES

RELATED APPLICATIONS

This application is divisional of U.S. Patent Application Ser. No. ("USSN") 12/766,092, filed Apr. 23, 2010, which was a continuation-in-part of U.S. Ser. No. 11/961,436, filed Dec. 20, 2007, which claimed the benefit under 35 U.S.C. §119(e) of provisional U.S. Patent Application Ser. No. 60/885,325, filed on Jan. 17, 2007. U.S. Ser. No. 12/766,092 was a continuation-in-part of U.S. Ser. No. 12/731,781 (now issued U.S. Pat. No. 8,003,111), filed Mar. 25, 2010, which claimed the benefit under 35 U.S.C. 119(e) of U.S. Provisional Patent Application 61/163,666, filed Mar. 26, 2009. U.S. Ser. No. 12/766,092 was a continuation-in-part of U.S. Ser. No. 12/644,146 (now issued U.S. Pat. No. 7,981,398), filed Dec. 22, 2009, which was a divisional of U.S. Ser. No. 11/925,408 (now issued U.S. Pat. No. 7,666,400), filed Oct. 26, 2007. U.S. Ser. No. 12/766,092 was a continuation-in-part of U.S. Ser. No. 12/417,917 (now issued U.S. Pat. No. 7,906,121), filed Apr. 3, 2009, which was a divisional of U.S. Ser. No. 11/478,021 (now issued U.S. Pat. No. 7,534,866), filed Jun. 29, 2006. U.S. Ser. No. 12/766,092 was a continuation-in-part of U.S. Ser. No. 12/396,965 (now issued U.S. Pat. No. 7,871,622), filed Mar. 3, 2009, which was a divisional of U.S. Ser. No. 11/391,584 (now issued U.S. Pat. No. 7,521,056), filed Mar. 28, 2006. U.S. Ser. No. 12/766,092 was a continuation-in-part of U.S. Ser. No. 12/396,605 (now issued U.S. Pat. No. 7,858,070), filed Mar. 3, 2009, which was a divisional of U.S. Ser. No. 11/633,729 (now issued U.S. Pat. No. 7,527,787), filed Dec. 5, 2006, which was a continuation-in-part of PCT/US06/010762, filed Mar. 24, 2006, PCT/US06/012084, filed Mar. 29, 2006, PCT/US06/025499, filed Jun. 29, 2006, U.S. Ser. No. 11/389,358 (now issued U.S. Pat. No. 7,550,143), filed Mar. 24, 2006, and claimed the benefit of U.S. Provisional Patent Applications 60/864,530, filed Nov. 6, 2006; 60/668,603, filed Apr. 6, 2005; 60/728,292, filed Oct. 19, 2005; 60/751,196, filed Dec. 16, 2005; and 60/782,332, filed Mar. 14, 2006. U.S. Ser. No. 12/766,092 was a continuation-in-part of U.S. Ser. No. 12/418,877 (now issued U.S. Pat. No. 7,906,118), filed Apr. 6, 2009, which claimed the benefit of U.S. Provisional Patent Applications 61/043,932, filed Apr. 10, 2008, 61/104,916, filed Oct. 13, 2008, and 61/119,542, filed Dec. 3, 2008. The text of each priority application cited above is incorporated herein by reference in its entirety.

BACKGROUND

Targeting of drugs, toxins, and radionuclides to disease sites using tumor-selective monoclonal antibodies (MAbs) is an evolving field of biopharmaceutical research, with three approved products impacting the practice of medicine (Sharkey R M and Goldenberg D M, CA Cancer J. Clin. 2006; 56:226-243).

Typically, a MAb for an antigen expressed on a disease site, such as that on the surface of a tumor cell, is modified with drugs or toxins or radionuclides to form immunoconjugates, and the latter are targeted in vivo. In the formation of immunoconjugates, only a limited number of modifying groups can be introduced on to the antibody without affecting the MAb's immunoreactivity. Moreover, many of these modifiers, such as drugs, are generally hydrophobic, and cause solubility problems if the substitution is increased beyond a threshold level. These problems have been addressed by loading drugs or other moieties on to a water-soluble polymer such as dextran, and subsequently covalently linking the drug-polymer to antibodies to the Fc region carbohydrates site-specifically. See Shih, et al., U.S. Pat. Nos. 4,699,784 and 5,057,313, both incorporated herein by reference in their entirety. The size of the directly conjugated antibody-polymer-drug construct can be an issue in certain applications, and an alternative approach to increasing the concentration of the drugs at the disease site, other than using a direct immunoconjugate, is desirable.

An approach that bypasses the limitations of using direct immunoconjugates, called 'pretargeting', makes use of a bi- or multispecific antibody with specificities for disease antigens as well as for a small molecular mass hapten (Goldenberg D M, et al., J Clin Oncol. 2006; 24: 823-834). In this method, the disease targeting step is temporally separated from the targeting of the drug molecule. Briefly, a bispecific or multispecific antibody is administered first to a patient. After the antibody localizes at the disease site by binding to disease-associated antigen, a second agent consisting of the drug attached to the small molecular mass hapten is administered. This drug-attached hapten selectively binds to the anti-hapten component of the bispecific antibody that has been pretargeted at the disease site. Generally, the second step agent is a small molecule, such as a peptide with hapten and drug attached to it, which clears rapidly from circulation, with a single or just a few passes at the tumor site where the material must be captured. In addition, the usual design of such second step agents results in only a few drug molecules attached. The combination of quick clearance and low drug substitution results in low specific activity of the drug at the disease site.

There thus exists a need for developing new methods for targeting a large number of therapeutic agents to disease sites selectively. A general method, applicable to both direct immunoconjugate as well as the second step agent of pretargeting approach, would be highly desirable.

SUMMARY

The present invention solves the aforementioned problems of direct or pretargeting mode of antibody-based delivery of therapeutics by providing a therapeutic-loaded polymer that is also covalently attached to a low molecular weight peptide. For application to pretargeting, the peptide moiety may contain one or two hapten units, such as HSG (histamine-succinyl-glycine). The use of bispecific antibodies for diagnosis and therapy, illustrated with anti-HSG antibody as one arm of the bispecific is well known in the art, and methods for the preparation of HSG-containing peptides are also described in the art (U.S. Pat. Nos. 7,138,103 and 7,172,751, both incorporated herein by reference in their entirety).

For use with direct immunoconjugates, the peptide may contain functional group(s) for covalent linking to bi- or multivalent antibodies, or fragments thereof, in a manner that does not affect the antigen-binding properties of antibodies. In a preferred embodiment, the peptide may be attached to bi- or multivalent antibodies or fragments thereof using the 'dock and lock (DNL)' technology (Rossi E A, et al., *Proc Natl Acad Sci USA* 2006; 103:6841-6846; U.S. Patent Application Publication Nos. 20060228300; 20070086942 and 20070140966, the text of each of which is incorporated herein by reference in its entirety). These and other aspects of the invention are described in detail below.

DETAILED DESCRIPTION

In preferred embodiments, the polymer, such as a dextran molecule, is derivatized to possess multiple carboxylic acid groups. A fraction of these carboxylic acid groups is derivatized by amide formation with ethylenediamine such that about one molecule of a maleimide-containing cross-linker is attached per molecule of the polymer. The remaining carboxylic acid groups are modified to possess a pre-determined level (substitution) of a functional group that is chemoselective for attachment to a drug. The substitution level of this functional group will determine the substitution level of drugs attached to the polymer.

In one embodiment, the functional group on the polymer is an acetylene moiety. The polymer-(alkyne)$_x$-peptide derivative is coupled with an azide-containing drug in a copper (+1)-catalyzed cycloaddition reaction called 'click chemistry' (Kolb H C and Sharpless K B, *Drug Discov Today* 2003; 8: 1128-37). Click chemistry takes place in aqueous solution at near-neutral pH conditions, and is thus amenable for drug conjugation. The advantage of click chemistry is that it is chemoselective, and complements other well-known conjugation chemistries such as the thiol-maleimide reaction. The attachment of drug to the polymer-peptide addend is carried out as a final step in the preparation of material for pretargeting. In the immunoconjugate formation in the context of the DNL approach, the drug can be attached to the polymer prior to DNL assembly. It can be also more advantageously performed as a final step after the DNL assembly, and this way the drug is not involved during the DNL process.

In another embodiment, the functional group on the polymer is a hydrazide. The drug such as doxorubicin, containing a keto group, can be coupled to the hydrazide-appended polymer at a pH in the range of 5-to-7.

In a third embodiment, the functional group on the polymer is a cyclodextrin molecule that can non-covalently bind to drugs by host-guest complexation.

In some embodiments, the polymer can be substituted with 2 or more drugs. This is particularly suited for the click chemistry approach whereby a single polymer addend with multiple alkyne moieties (usually monosubstituted acetylenes) can be first coupled with one azide-containing drug. By limiting the molar equivalents, only a certain fraction of the acetylene groups are derivatized by the first drug-azide. The process is repeated with a second azide-containing drug so that the remaining acetylene groups are coupled. For example, the first drug can be doxorubicin which is a topoisomerase II inhibitor, and the second drug can be SN-38 which is a topoisomerase I inhibitor.

When attached to the polymer by the click chemistry method, the bonding is via a stable triazole. A cleavable linker may additionally be built into the cross-linker between the drug and the azide to enable drug release.

Embodiments with respect to the nature of the 'recognition moiety' are as follows: (1) It can be a peptide containing one or 2 molecules of a hapten such as HSG or DTPA, that binds specifically to anti-HSG or anti-DTPA antibodies, respectively. The drug-polymer-hapten can then be used in a pretargeting mode after first targeting the disease site with a bi- or multispecific antibody possessing at least one arm specific for the disease site and at least one arm specific for the hapten. Alternatively, a pre-complexed multispecific antibody-polymer-hapten may be utilized within the scope of this invention. (2) It can be folic acid, such that the polymer-drug-folate complex is used to target folate receptors on disease sites such as in cancers, in as much as targeting of folate receptors using folate-appended diagnostic or therapeutic moieties is a well known strategy. (3) It can be a peptide such as somatostatin (SS) or VIP peptide, useful for receptor-targeting at disease sites. (4) It can be biotin, for use in avidin/streptavidin-based pretargeting protocols. (5) It can be a complementary anti-sense oligonucleotide. (6) It can be the anchoring domain (AD) peptide of the 'dock and lock' (DNL) methodology (see, e.g., U.S. patent application Ser. No. 11/389,358, filed Mar. 24, 2006; Ser. No. 11/391,584, filed Mar. 28, 2006; Ser. No. 11/478,021, filed Jun. 29, 2006; and Ser. No. 11/633,729, filed Dec. 5, 2006, each incorporated herein by reference in its entirety). The components specific for the 'recognition moieties' and part of the bi- or multispecific antibodies used in pretargeting protocol using embodiments 1 through 5 described in this paragraph are anti-HSG or anti-DTPA antibody; anti-folate antibody; anti-somatostatin antibody; avidin/streptavidin; or oligonucleotide, respectively. The counterpart component of the sixth embodiment is defined by the nature of the DNL methodology and for the AD sequence would be a complementary DDD sequence. In embodiments 2 and 3, the polymer-drug-folate or polymer-drug-SS can latch on to the bi- or multispecific antibody pretargeted at the disease site and also target the folate or SS receptors, respectively, thereby augmenting the mechanisms of targeting at the disease sites. The number of such recognition moieties introduced on to the polymer is preferably 1-10, more preferably 1-5, and most preferably 1-2. The number of recognition moieties per polymer is preferably 1 when using in the context of DNL assemblage, but can be greater than 1 when used in pretargeting formats.

Examples of drug-dextran are shown below. Scheme 1 gives a general approach to modification of polymer using acetylene-azide coupling chemistry, and is illustrated by structures 1 through 3.

Scheme-1

Step-1:

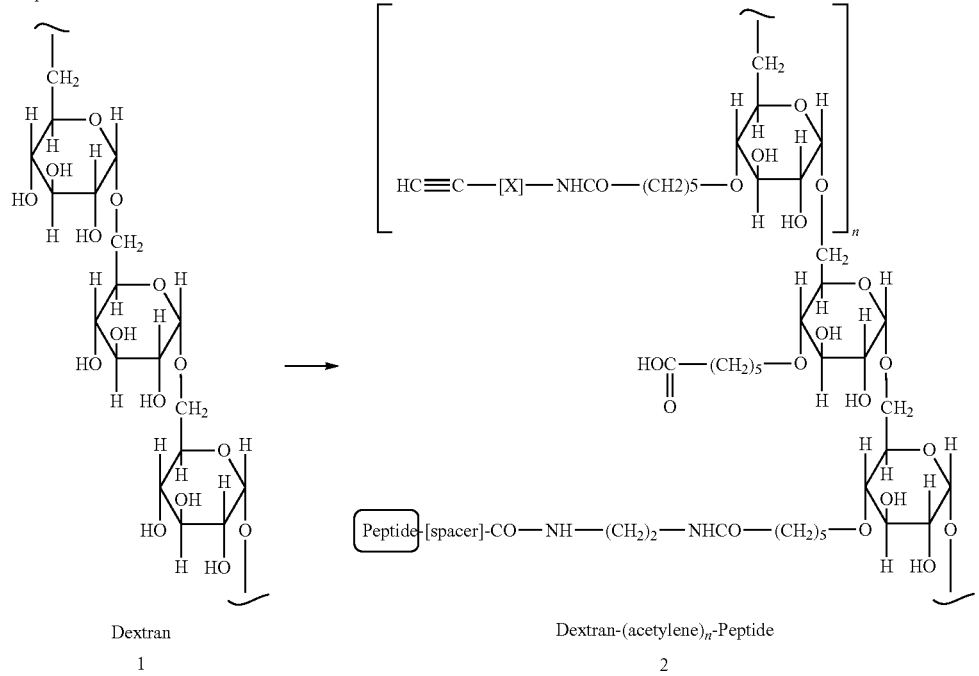

Dextran                                              Dextran-(acetylene)$_n$-Peptide
1                                                         2

Step-2:

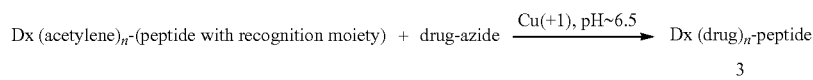

3

Alternatively, the polymer can be derivatized to contain an azide group in place of acetylene, and the drug can be derivatized with acetylene group instead of azide.

Structure 4: This represents one type of linking by the 'click chemistry' to one type of drug. In this, 'Rm' is a recognition moiety, n=0~16, x=10-1000, and '(Z)' is additional spacer consisting of $(CH_2)_m$—NH—CO moiety, where m is an integer with values of 1-20, preferably 1-5, and most preferably 1.

Structure-4

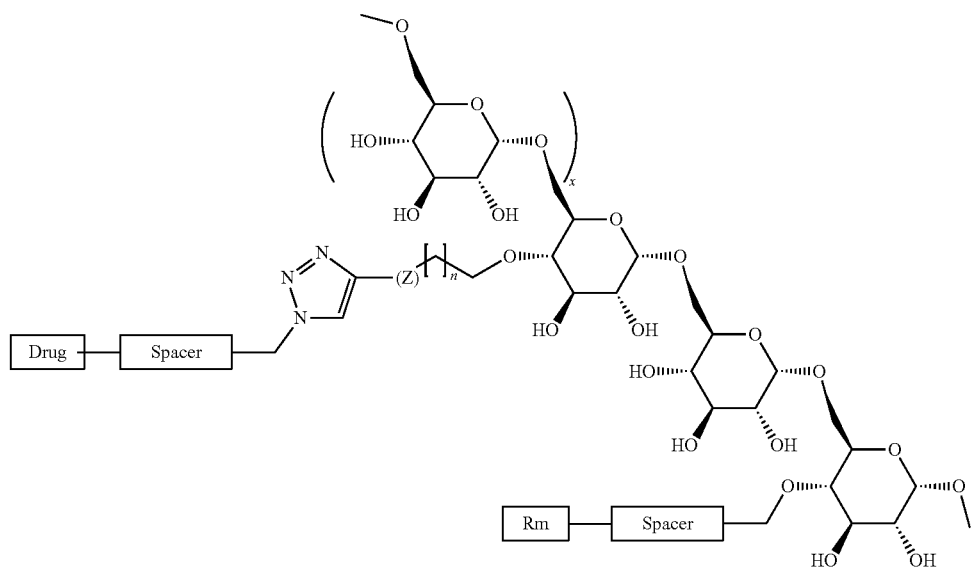

Structure 5: This represents one type of linking by the 'click chemistry' to 2 types of drugs (the 'recognition' moiety indicated by am'). Drug-1 can be an anthracycline drug, such as doxorubicin, which is a topoisomerase II inhibitor, while the second drug can be a camptothecin, such as SN-38, which is a topoisomerase I inhibitor. In this example, 'x' is the repeating dextran unit defined by the polymer size, 'n' is the number of moieties derivatized with drug 1 and drug 2, which defines the level of drug loading, and 'Z' is spacer. Although shown in this structure as 'n' for both drug 1 and drug 2, the value of 'n' can differ for drug 1 and drug 2 for different levels of the drug loadings. The acetylene-azide coupling results in a triazole structural moiety as shown. The spacer 1 and spacer 2 contain cleavable linker part. The cleavable linker can be an acid-cleavable hydrazone or cathepsin B cleavable peptide in the case of anthracycline such as doxorubicin, and it can be an ester or carbonate bond and/or a cathepsin B cleavable peptide in the case of a camptothecin. The drugs can be other than that indicated, and the multiplicity of drug types is not limited to 2. [In this structure, 'Rm' is a recognition moiety, n=0~16, x=10-1000, and '(Z)' is additional spacer consisting of $(CH_2)_m$—NH—CO moiety, where m is an integer with values of 1-20, preferably 1-5, and most preferably 1.]

Structure-5

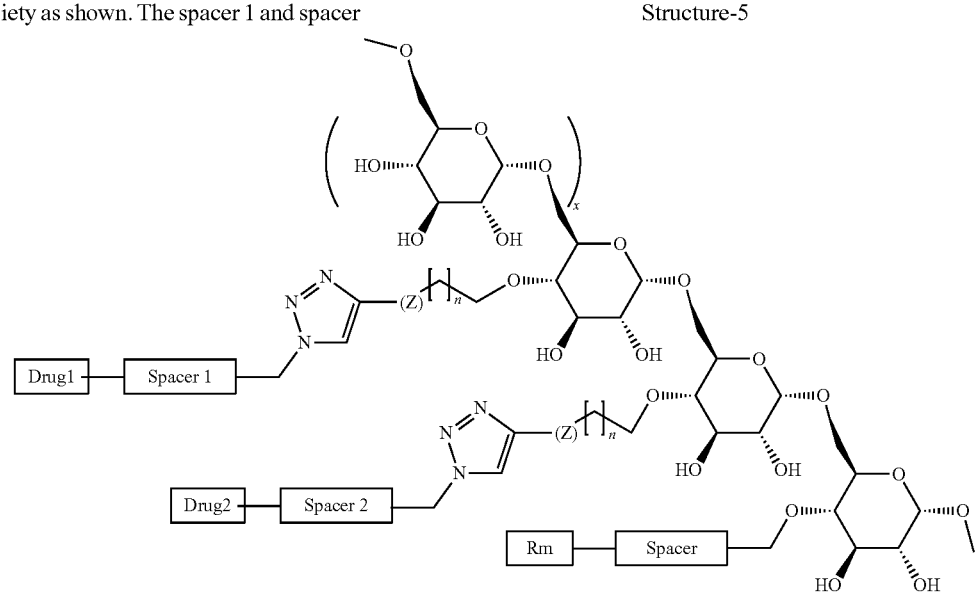

Structure 6: This is an example of chemoselective modification of dextran. In this example of 70 KD MW dextran, 44 COOH groups are first introduced by reacting with 6-bromo-hexanoic acid, representing '11%' of monomeric unit (or 44 moieties) modified. Of these, 20 available COOH groups ('5%' of monomeric units) are converted to Boc-protected hydrazide using BOC—$NHNH_2$ and water soluble carbodiimide, EDC. The remaining COOH groups are partly converted to terminate in an amine, using ethylene diamine and EDC coupling, such that 8 amines are substituted per polymer. Conditions have been developed to substitute just one of these amino groups with a modifier, such as pyridyldithio group of structure 7, for later attachment to a peptide.

Structure-6

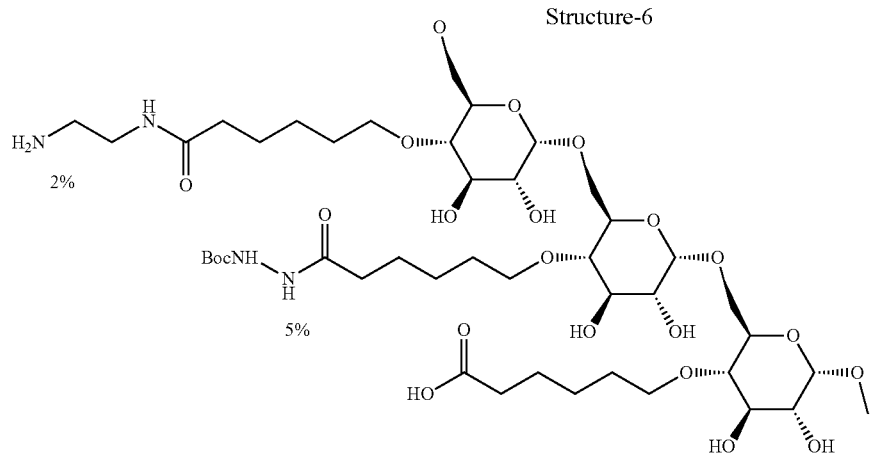

Structure 7: This structure shows that an average of one SPDP molecule can be substituted on to the 70 kD dextran. By first reacting with a thiol-containing peptide in a diulfide-exchange reaction, an average of one peptide can be introduced. Alternatively, the disulfide of structure 7 can be reduced with dithiothreitol or TCEP, and the thiol-containing dextran can be reacted with a maleimide-containing peptide. Yet another variation is that the amine on dextran is derivatized with a maleimide-containing cross-linker for further reaction with a thiol-containing peptide. The peptide moiety contains one or two hapten molecules, such as HSG, or it is 'AD' peptide suitable for fusing with 'DDD' component of DNL methodology. BOC-deprotection under acidic conditions then liberates hydrazide, suitable for reacting with aldehyde or keto group on a drug. Alternatively, and more preferably in the DNL approach, the hydrazide moiety is replaced by acetylene group that can be later coupled to azide-containing drug. An advantage in this approach is that the DNL assembly can be first performed, and the resultant assembly will contain drug signatures, which are actually the acetylene (or azide) groups. The DNL product can be reacted chemoselectively with an azide (or acetylene)-appended drug. An advantage of pre-assembly of DNL product is that the drug can be defined subsequently. And, for each assembly, containing a defined multivalent antibody component, one could substitute different drug types by using the corresponding azide-derivatized drugs.

While the nature of 'recognition moiety' is defined in the DNL product as 'AD' peptide, it can be variable in other examples as enumerated in a previous section.

Structure-7

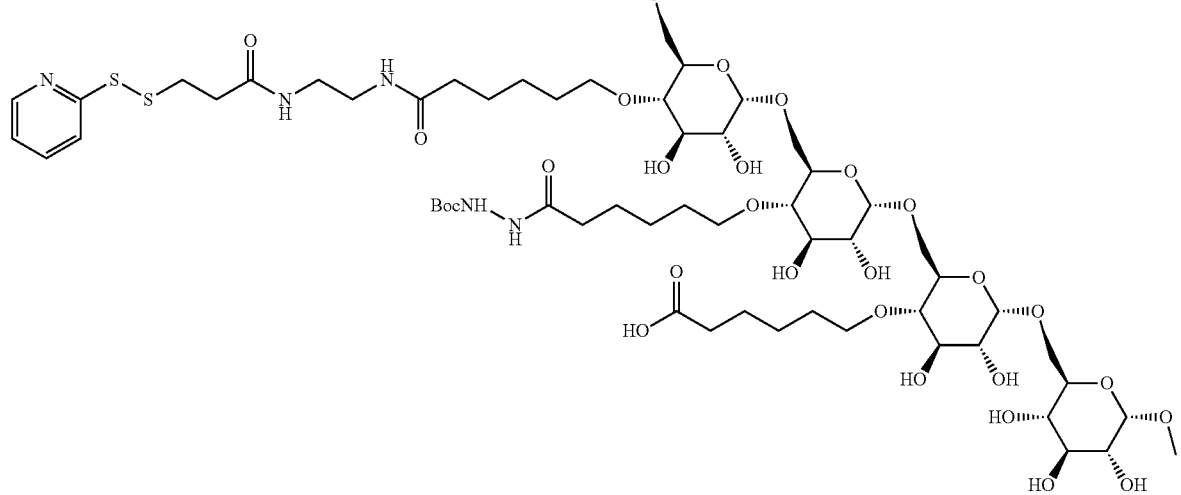

Structure 8: This is a variation of structure 2, showing the substitution on dextran of cyclodextrin instead of acetylene. A suitable drug, such as doxorubicin, capable of forming non-covalent complex with cyclodextrin is subsequently added. Cyclodextrin substitution determines drug substitution. [In this structure, 'Rm' is a recognition moiety, n=0~16, x=10-1000, and '(Z)' is additional spacer consisting of $(CH_2)_m$—NH—CO moiety, where m is an integer with values of 1-20, preferably 1-5, and most preferably 1.]

Structure-8

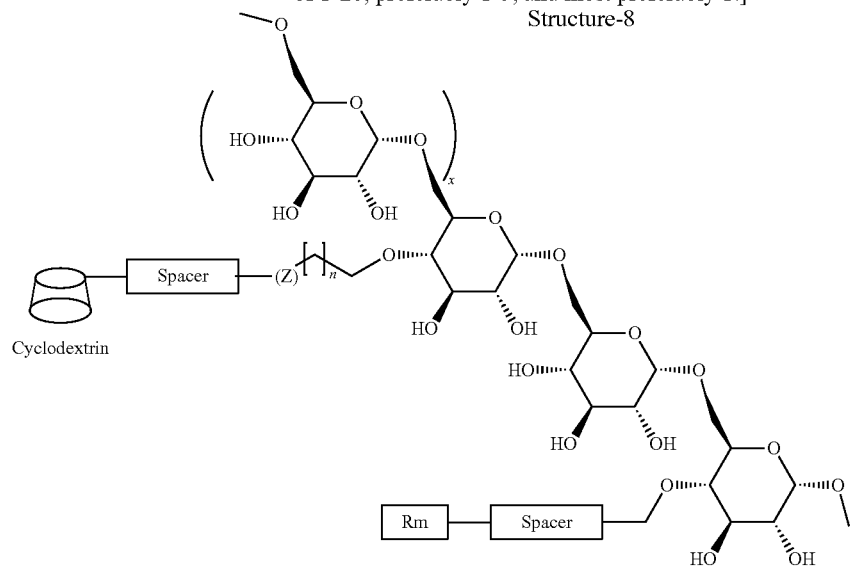

Structure 9: This is a variation of structure 5, showing the substitution on dextran of one drug via 'click chemistry' and the substitution of cyclodextrin for complexation with a second drug. As in other illustrations, 'Rm' is a recognition moiety, n=0~16, x=10-1000, and '(Z)' is additional spacer consisting of $(CH_2)_m$—NH—CO moiety, where m is an integer with values of 1-20, preferably 1-5, and most preferably 1.

Structure-9

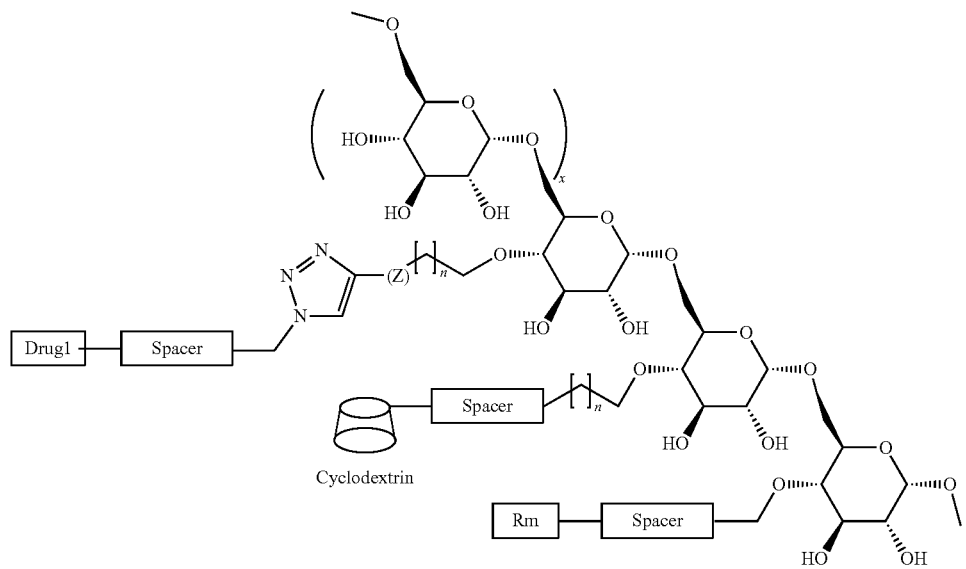

Polymers

Water-soluble polymers such as dextran, polyglutamic acid, dendrimers, and so on, are within the scope of the invention. Although exemplified with dextran, the polymer component is not limited to dextran. Polyglutamic acid already has carboxylic acid groups in it, and so it is equivalent to the carboxylic acid-added dextran from the viewpoint of this disclosure. Whatever strategies are described for COOH-added dextran are equally applicable for polyglutamic acid. With different generation dendrimers, functional groups are derivatized sequentially to contain drug signatures such as alkyne or azide derivatizable with azide-drug or alkyne-drug, respectively, and other derivatives that can be coupled to bifunctional drug derivatives.

Therapeutic Agents

Therapeutic agents for use in this invention include, for example, chemotherapeutic drugs such as vinca alkaloids, anthracyclines, epidophyllotoxins, taxanes, antimetabolites, alkylating agents, antibiotics, Cox-2 inhibitors, antimitotics, antiangiogenic and proapoptotic agents, particularly doxorubicin, methotrexate, taxol, camptothecins, and others from these and other classes of anticancer agents, and the like. Other cancer chemotherapeutic drugs include nitrogen mustards, alkyl sulfonates, nitrosoureas, triazenes, folic acid analogs, pyrimidine analogs, purine analogs, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Exemplary drugs of use may include 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosurea, plicomycin, procarbazine, paclitaxel, pentostatin, PSI-341, raloxifene, semustine, streptozocin, tamoxifen, taxol, temazolomide (an aqueous form of DTIC), transplatinum, thalidomide, thioguanine, thiotepa, teniposide, topotecan, uracil mustard, vinorelbine, vinblastine, vincristine and vinca alkaloids.

Toxins of use may include ricin, abrin, alpha toxin, saporin, ribonuclease (RNase), e.g., onconase, DNase I, *Staphylococcal* enterotoxin-A, pokeweed antiviral protein, gelonin, diphtheria toxin, *Pseudomonas* exotoxin, and *Pseudomonas* endotoxin.

Chemokines of use may include RANTES, MCAF, MIP1-alpha, MIP1-Beta and IP-10.

In certain embodiments, anti-angiogenic agents, such as angiostatin, baculostatin, canstatin, maspin, anti-VEGF antibodies, anti-PlGF peptides and antibodies, anti-vascular growth factor antibodies, anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide (roquinimex), thalidomide, pentoxifylline, genistein, TNP-470, endostatin, paclitaxel, accutin, angiostatin, cidofovir, vincristine, bleomycin, AGM-1470, platelet factor 4 or minocycline may be of use.

Other useful therapeutic agents may comprise oligonucleotides, especially antisense oligonucleotides that preferably are directed against oncogenes and oncogene products, such as bcl-2 or p53. A preferred form of therapeutic oligonucleotide is siRNA.

Targeting Moieties

In one embodiment, the targeting moiety may be a multivalent and/or multispecific MAb. In another embodiment, the targeting moiety is multivalent antibody fragment made with DNL (dock-and-lock) methodology. The targeting moiety may be a murine, chimeric, humanized, or human monoclonal antibody, and said antibody is in intact, fragment (Fab, Fab', F(ab)$_2$, F(ab')$_2$), or sub-fragment (single-chain constructs) form.

In a preferred embodiment, the targeting moiety is reactive with an antigen or epitope of an antigen expressed on a cancer or malignant cell. The cancer cell is preferably a cell from a hematopoietic tumor, carcinoma, sarcoma, melanoma or a glial tumor.

The targeting moiety is preferably an antibody (including fully human, non-human, humanized, or chimeric antibodies) or an antibody fragment (including enzymatically or recombinantly produced fragments) and binding proteins incorporating sequences from antibodies or antibody fragments. The antibodies, fragments, and binding proteins may be multivalent and multispecific or multivalent and monospecific as defined above.

In a preferred embodiment, antibodies, such as MAbs, are used that recognize or bind to markers or tumor-associated antigens that are expressed at high levels on target cells and that are expressed predominantly or only on diseased cells versus normal tissues, and antibodies that internalize rapidly. Antibodies useful within the scope of the present invention include MAbs with properties as described above (and show distinguishing properties of different levels of internalization into cells and microorganisms), and contemplate the use of, but are not limited to, in cancer, the following MAbs: LL1 (anti-CD74), LL2 and RFB4 (anti-CD22), RS7 (anti-epithelial glycoprotein-1 (EGP-1)), PAM-4 and KC4 (both anti-MUC1), MN-14 (anti-carcinoembryonic antigen (CEA, also known as CD66e), Mu-9 (anti-colon-specific antigen-p), Immu 31 (an anti-alpha-fetoprotein), TAG-72 (e.g., CC49), Tn, J591 (anti-PSMA (prostate-specific membrane antigen)), G250 (an anti-carbonic anhydrase IX MAb) and L243 (anti-HLA-DR). Other useful antigens that may be targeted using these conjugates include HER-2/neu, BrE3, CD19, CD20 (e.g., C2B8, hA20, 1F5 MAbs) CD21, CD23, CD37, CD45, CD74, CD80, alpha-fetoprotein (AFP), VEGFR (e.g. Avastin®, fibronectin splice variant), ED-B (e.g., L19), EGF receptor or ErbB1 (e.g., Erbitux®), ErbB2, ErbB3, placental growth factor (PlGF), MUC1, MUC2, MUC3, MUC4, PSMA, gangliosides, HCG, EGP-2 (e.g., 17-1A), CD37, HLA-DR, CD30, Ia, A3, A33, Ep-CAM, KS-1, Le(y), S100, PSA (prostate-specific antigen), tenascin, folate receptor, Thomas-Friedenreich antigens, tumor necrosis antigens, tumor angiogenesis antigens, Ga 733, IL-2, IL-6, T101, MAGE, insulin-like growth factor (ILGF), migration inhibition factor (MIF), the HLA-DR antigen to which L243 binds, CD66 antigens, i.e. CD66a-d or a combination thereof. The CD66 antigens consist of five different glycoproteins with similar structures, CD66a-e, encoded by the carcinoembryonic antigen (CEA) gene family members, BCG, CGM6, NCA, CGM1 and CEA, respectively. These CD66 antigens are expressed mainly in granulocytes, normal epithelial cells of the digestive tract and tumor cells of various tissues. A number of the aforementioned antigens are disclosed in U.S. Provisional Application Ser. No. 60/426,379, entitled "Use of Multi-specific, Non-covalent Complexes for Targeted Delivery of Therapeutics," filed Nov. 15, 2002, incorporated herein by reference.

Exemplary anti-cancer antibodies that may be utilized include, but are not limited to, hR1 (anti-IGF-1R, U.S. Provisional Patent Application Ser. No. 61/145,896, filed Jan. 20, 2009) hPAM4 (anti-MUC1, U.S. Pat. No. 7,282,567), hA20 (anti-CD20, U.S. Pat. No. 7,251,164), hA19 (anti-CD19, U.S. Pat. No. 7,109,304), hIMMU31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEA, U.S. Pat. No. 6,676,924), hMN-15 (anti-CEA, U.S. patent application Ser. No. 10/672,278), hRS7 (anti-EGP-1, U.S. Pat. No. 7,238,785) and hMN-3 (anti-CEA, U.S. Pat. No. 7,541,440) the Examples section of each cited patent or application incorporated herein by reference. The skilled artisan will realize that this list is not limiting and any other known antibody may be utilized in the claimed methods and compositions.

Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206'; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767;

6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

In another preferred embodiment of the present invention involving polymer-therapeutic-recognition moiety precomplexed or fused by the DNL methodology, antibodies are used that internalize rapidly and are then re-expressed, processed and presented on cell surfaces, enabling continual uptake and accretion of circulating conjugate by the cell. An example of a most-preferred antibody/antigen pair is LL1, an anti-CD74 MAb (invariant chain, class II-specific chaperone, Ii). The CD74 antigen is highly expressed on B-cell lymphomas, certain T-cell lymphomas, melanomas and certain other cancers (Ong et al., *Immunology* 98:296-302 (1999)), as well as certain autoimmune diseases. This embodiment is particularly preferred as a pre-complexed or DNL construct incorporating polymer-therapeutic-recognition moiety.

In various embodiments, a conjugate as disclosed herein may be part of a composite, multispecific antibody. Such antibodies may contain two or more different antigen binding sites, with differing specificities. The multispecific composite may bind to different epitopes of the same antigen, or alternatively may bind to two different antigens. Some of the more preferred target combinations include the following. This is a list of examples of preferred combinations, but is not intended to be exhaustive.

TABLE 1

Some Examples of multispecific antibodies

| First target | Second target |
| --- | --- |
| MIF | A second proinflammatory effector cytokine, especially HMGB-1, TNF-α, IL-1, or IL-6 |
| MIF | Proinflammatory effector chemokine, especially MCP-1, RANTES, MIP-1A, or MIP-1B |
| MIF | Proinflammatory effector receptor, especially IL-6R IL-13R, and IL-15R |
| MIF | Coagulation factor, especially TF or thrombin |
| MIF | Complement factor, especially C3, C5, C3a, or C5a |
| MIF | Complement regulatory protein, especially CD46, CD55, CD59, and mCRP |
| MIF | Cancer associated antigen or receptor |
| HMGB-1 | A second proinflammatory effector cytokine, especially MIF, TNF-α, IL-1, or IL-6 |
| HMGB-1 | Proinflammatory effector chemokine, especially MCP-1, RANTES, MIP-1A, or MIP-1B |
| HMGB-1 | Proinflammatory effector receptor especially MCP-1, RANTES, MIP-1A, or MIP-1B |
| HMGB-1 | Coagulation factor, especially TF or thrombin |
| HMGB-1 | Complement factor, especially C3, C5, C3a, or C5a |
| HMGB-1 | Complement regulatory protein, especially CD46, CD55, CD59, and mCRP |
| HMGB-1 | Cancer associated antigen or receptor |
| TNF-α | A second proinflammatory effector cytokine, especially MIF, HMGB-1, TNF-α, IL-1, or IL-6 |
| TNF-α | Proinflammatory effector chemokine, especially MCP-1, RANTES, MIP-1A, or MIP-1B |
| TNF-α | Proinflammatory effector receptor, especially IL-6R IL-13R, and IL-15R |
| TNF-α | Coagulation factor, especially TF or thrombin |
| TNF-α | Complement factor, especially C3, C5, C3a, or C5a |
| TNF-α | Complement regulatory protein, especially CD46, CD55, CD59, and mCRP |
| TNF-α | Cancer associated antigen or receptor |
| LPS | Proinflammatory effector cytokine, especially MIF, HMGB-1, TNF-α, IL-1, or IL-6 |
| LPS | Proinflammatory effector chemokine, especially MCP-1, RANTES, MIP-1A, or MIP-1B |
| LPS | Proinflammatory effector receptor, especially IL-6R IL-13R, and IL-15R |
| LPS | Coagulation factor, especially TF or thrombin |
| LPS | Complement factor, especially C3, C5, C3a, or C5a |
| LPS | Complement regulatory protein, especially CD46, CD55, CD59, and mCRP |
| TF or thrombin | Proinflammatory effector cytokine, especially MIF, HMGB-1, TNF-α, IL-1, or IL-6 |
| TF or thrombin | Proinflammatory effector chemokine, especially MCP-1, RANTES, MIP-1A, or MIP-1B |
| TF or thrombin | Proinflammatory effector receptor, especially IL-6R IL-13R, and IL-15R |
| TF or thrombin | Complement factor, especially C3, C5, C3a, or C5a |
| TF or thrombin | Complement regulatory protein, especially CD46, CD55, CD59, and mCRP |
| TF or thrombin | Cancer associated antigen or receptor |

Still other combinations, such as are preferred for cancer therapies, include CD20+CD22 antibodies, CD74+CD20 antibodies, CEACAM5 (CEA)+CEACAM6 antibodies, insulin-like growth factor (ILGF)+CEACAM5 antibodies, EGP-1 (e.g., RS-7)+ILGF antibodies, CEACAM5+EGFR antibodies. Such antibodies need not only be used in combination, but can be combined as fusion proteins of various forms, such as IgG, Fab, scFv, and the like, as described in U.S. Pat. Nos. 6,083,477; 6,183,744 and 6,962,702 and U.S. Patent Application Publication Nos. 20030124058; 20030219433; 20040001825; 20040202666; 20040219156; 20040219203; 20040235065; 20050002945; 20050014207; 20050025709; 20050079184; 20050169926; 20050175582; 20050249738; 20060014245 and 20060034759, each of which is incorporated herein by reference in their entirety.

In certain embodiments, the binding moieties described herein may comprise one or more avimer sequences. Avimers are a class of binding proteins somewhat similar to antibodies in their affinities and specificities for various target molecules. They were developed from human extracellular receptor domains by in vitro exon shuffling and phage display. (Silverman et al., 2005, Nat. Biotechnol. 23:1493-94; Silverman et al., 2006, Nat. Biotechnol. 24:220.) The resulting multidomain proteins may comprise multiple independent binding domains, which may exhibit improved affinity (in some cases sub-nanomolar) and specificity compared with single-epitope binding proteins. (Id.) In various embodiments, avimers may be attached to, for example, AD and/or DDD sequences for use in the claimed methods and compositions, as described in provisional U.S. Patent Application Ser. Nos. 60/668,603, filed Apr. 6, 2005 and 60/751,196, filed Dec. 16, 2005, each incorporated herein in their entirety by reference. Additional details concerning methods of construction and use of avimers are disclosed, for example, in U.S. Patent Application Publication Nos. 20040175756, 20050048512, 20050053973, 20050089932 and 20050221384, the Examples section of each of which is incorporated herein by reference.

In a preferred embodiment, an intracellularly-cleavable moiety incorporated in the 'drug-polymer-recognition moiety' may be cleaved after its conjugate with the pretargeted multispecific antibody, or its non-covalent complex with the multispecific antibody, or a covalent DNL construct is internalized into the cell, and particularly cleaved by esterases and peptidases or by pH-dependent processes or by disulfide reduction.

Therapeutic Methods

Another embodiment relates to a method of treating a subject, comprising administering a therapeutically effective amount of a therapeutic conjugate of the preferred embodiments of the present invention to a subject. Diseases that may be treated with the therapeutic conjugates of the preferred embodiments include, but are not limited to B-cell malignancies (e.g., non-Hodgkin's lymphoma and chronic lymphocytic leukemia using, for example LL2 MAb; see U.S. Pat. No. 6,183,744), adenocarcinomas of endodermally-derived digestive system epithelia, cancers such as breast cancer and non-small cell lung cancer, and other carcinomas, sarcomas, glial tumors, myeloid leukemias, etc. In particular, antibodies against an antigen, e.g., an oncofetal antigen, produced by or associated with a malignant solid tumor or hematopoietic neoplasm, e.g., a gastrointestinal, lung, breast, prostate, ovarian, testicular, brain or lymphatic tumor, a sarcoma or a melanoma, are advantageously used. Such therapeutics can be given once or repeatedly, depending on the disease state and tolerability of the conjugate, and can also be used optimally in combination with other therapeutic modalities, such as surgery, external radiation, radioimmunotherapy, immunotherapy, chemotherapy, antisense therapy, interference RNA therapy, gene therapy, and the like. Each combination will be adapted to the tumor type, stage, patient condition and prior therapy, and other factors considered by the managing physician.

As used herein, the term "subject" refers to any animal (i.e., vertebrates and invertebrates) including, but not limited to mammals, including humans. The term subject also includes rodents (e.g., mice, rats, and guinea pigs). It is not intended that the term be limited to a particular age or sex. Thus, adult and newborn subjects, as well as fetuses, whether male or female, are encompassed by the term.

In various embodiments, antibodies against known tumor-associated antigens as described above may be utilized for therapy of diseases, such as cancer. For example, the diseases that are preferably treated with anti-CD74 antibodies include, but are not limited to, non-Hodgkin's lymphoma, Hodgkin's disease, melanoma, lung cancer, myeloid leukemias, and multiple myeloma. Continual expression of the CD74 antigen for short periods of time on the surface of target cells, followed by internalization of the antigen, and re-expression of the antigen, enables the targeting LL1 antibody to be internalized along with any chemotherapeutic moiety it carries. This allows a high, and therapeutic, concentration of LL1-chemotherapeutic drug conjugate to be accumulated inside such cells. Internalized LL1-chemotherapeutic drug conjugates are cycled through lysosomes and endosomes, and the chemotherapeutic moiety is released in an active form within the target cells.

In another preferred embodiment, therapeutic conjugates comprising the Mu-9 MAb can be used to treat colorectal, as well as pancreatic and ovarian cancers as disclosed in U.S. application Ser. No. 10/116,116, filed Apr. 5, 2002 and by Gold et al. (*Cancer Res*. 50: 6405 (1990), and references cited therein). In addition, the therapeutic conjugates comprising the PAM-4 MAb can be used to treat pancreatic cancer, as disclosed in U.S. Provisional Application Ser. No. 60/388,314, filed Jun. 14, 2002.

In another preferred embodiment, the therapeutic conjugates comprising the RS-7 MAb can be used to treat carcinomas such as carcinomas of the lung, stomach, urinary bladder, breast, ovary, uterus, and prostate, as disclosed in U.S. Provisional Application Ser. No. 60/360,229, filed Mar. 1, 2002 and by Stein et al. (*Cancer Res*. 50: 1330 (1990) and *Antibody Immunoconj. Radiopharm*. 4: 703 (1991)).

In another preferred embodiment, the therapeutic conjugates comprising the anti-AFP MAb can be used to treat hepatocellular carcinoma, germ cell tumors, and other AFP-producing tumors using humanized, chimeric and human antibody forms, as disclosed in U.S. Provisional Application Ser. No. 60/399,707, filed Aug. 1, 2002.

In another preferred embodiment, the therapeutic conjugates comprising anti-tenascin antibodies can be used to treat hematopoietic and solid tumors and conjugates comprising antibodies to Le(y) can be used to treat solid tumors.

In a preferred embodiment, the antibodies that are used in the treatment of human disease are human or humanized (CDR-grafted) versions of antibodies; although murine and chimeric versions of antibodies can be used. Same species IgG molecules as delivery agents are mostly preferred to minimize immune responses. This is particularly important when considering repeat treatments. For humans, a human or humanized IgG antibody is less likely to generate an anti-IgG immune response from patients. Antibodies such as hLL1 and hLL2 rapidly internalize after binding to internalizing antigen on target cells, which means that the chemotherapeutic drug being carried is rapidly internalized into cells as well. However, antibodies that have slower rates of internalization can also be used to effect selective therapy with this invention.

In another preferred embodiment, the therapeutic conjugates can be used against pathogens, since antibodies against pathogens are known. For example, antibodies and antibody fragments which specifically bind markers produced by or associated with infectious lesions, including viral, bacterial, fungal and parasitic infections, for example caused by pathogens such as bacteria, *rickettsia*, mycoplasma, protozoa, fungi, and viruses, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361,544, 4,468,457, 4,444,744, 4,818,709 and 4,624,846, and in Reichert and Dewitz, cited above. In a preferred embodiment, the pathogens are selected from the group consisting of HIV virus causing AIDS, *Mycobacterium tuberculosis, Streptococcus agalactiae*, methicillin-resistant *Staphylococcus aureus, Legionella pneumophilia, Streptococcus pyogenes, Escherichia coli, Neisseria gonorrhosae, Neisseria meningitidis, Pneumococcus, Hemophilis influenzae B, Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reo virus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Theileria parva, Taenia hydatigena, Taenia*

*ovis, Taenia saginata, Echinococcus granulosus, Mesocestoides corti, Mycoplasma arthritidis, M. hyorhinis, M. orale, M. arginini, Acholeplasma laidlawii, M. salivarium* and *M. pneumoniae*, as disclosed in U.S. Pat. No. 6,440,416.

In a more preferred embodiment, drug conjugates comprising anti-gp120 and other such anti-HIV antibodies can be used as therapeutics for HIV in AIDS patients; and drug conjugates of antibodies to *Mycobacterium tuberculosis* are suitable as therapeutics for drug-refractive tuberculosis. Fusion proteins of anti-gp120 MAb (anti HIV MAb) and a toxin, such as *Pseudomonas* exotoxin, have been examined for antiviral properties (Van Oigen et al., *J Drug Target*, 5:75-91, 1998)). Attempts at treating HIV infection in AIDS patients failed possibly due to insufficient efficacy or unacceptable host toxicity. The drug conjugates of the present invention advantageously lack such toxic side effects of protein toxins, and are therefore advantageously used in treating HIV infection in AIDS patients. These drug conjugates can be given alone or in combination with other antibiotics or therapeutic agents that are effective in such patients when given alone.

In another preferred embodiment, diseases that may be treated using the therapeutic conjugates include, but are not limited to immune dysregulation disease and related autoimmune diseases, including Class III autoimmune diseases such as immune-mediated thrombocytopenias, such as acute idiopathic thrombocytopenic purpura and chronic idiopathic thrombocytopenic purpura, dermatomyositis, Sjögren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis ubiterans, Sjögren's syndrome, primary biliary cirrhosis, Hashimoto's thyroiditis, thyrotoxicosis, scleroderma, chronic active hepatitis, rheumatoid arthritis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis, and also juvenile diabetes, as disclosed in U.S. Provisional Application Ser. No. 60/360,259, filed Mar. 1, 2002. Typical antibodies useful in these diseases include, but are not limited to, those reactive with HLA-DR antigens or B-cell or T-cell antigens (e.g., CD19, CD20, CD21, CD22, CD23, CD4, CD5, CD8, CD14, CD15, CD19, CD20, CD21, CD22, CD23, CD25, CD33, CD37, CD38, CD40, CD40L, CD46, CD52, CD54, CD74, CD80, CD126, B7, MUC1, Ia, HM1.24, and HLA-DR). Since many of these autoimmune diseases are affected by autoantibodies made by aberrant B-cell populations, depletion of these B-cells by therapeutic conjugates involving such antibodies bound with the drugs used in this invention, is a preferred method of autoimmune disease therapy, especially when B-cell antibodies are combined, in certain circumstances, with HLA-DR antibodies and/or T-cell antibodies (including those which target IL-2 as an antigen, such as anti-TAC antibody). In a preferred embodiment, the anti-B-cell, anti-T-cell, or anti-macrophage or other such antibodies of use in the treatment of patients with autoimmune diseases also can be conjugated to result in more effective therapeutics to control the host responses involved in said autoimmune diseases, and can be given alone or in combination with other therapeutic agents, such as TNF inhibitors or TNF antibodies, unconjugated B- or T-cell antibodies, and the like.

In a preferred embodiment, diseases that may be treated using the therapeutic conjugates include cardiovascular diseases, such as fibrin clots, atherosclerosis, myocardial ischemia and infarction. Antibodies to fibrin are known and in clinical trials as imaging agents for disclosing said clots and pulmonary emboli, while anti-granulocyte antibodies, such as MN-3, MN-15, NCA95, and CD15 antibodies, can target myocardial infarcts and myocardial ischemia, while anti-macrophage, anti-low-density lipoprotein (LDL), and anti-CD74 (e.g., hLL1) antibodies can be used to target atherosclerotic plaques.

In yet another preferred embodiment, diseases that may be treated using the therapeutic conjugates include neurodegenerative diseases characterized by a specific lesions against which a targeting moiety can be used, such as amyloid or beta-amyloid associated with Alzheimer's disease, and which serves as a target for localizing antibodies.

In a preferred embodiment, a more effective incorporation into cells and pathogens can be accomplished by using multivalent, multispecific or multivalent, monospecific antibodies. Multivalent means the use of several binding arms against the same or different antigen or epitope expressed on the cells, whereas multispecific antibodies involve the use of multiple binding arms to target at least two different antigens or epitopes contained on the targeted cell or pathogen. Examples of such bivalent and bispecific antibodies are found in U.S. patent applications 60/399,707, filed Aug. 1, 2002; 60/360, 229, filed Mar. 1, 2002; 60/388,314, filed Jun. 14, 2002; and 10/116,116, filed Apr. 5, 2002, all of which are incorporated by reference herein. These multivalent or multispecific antibodies are particularly preferred in the targeting of cancers and infectious organisms (pathogens), which express multiple antigen targets and even multiple epitopes of the same antigen target, but which often evade antibody targeting and sufficient binding for immunotherapy because of insufficient expression or availability of a single antigen target on the cell or pathogen. By targeting multiple antigens or epitopes, said antibodies show a higher binding and residence time on the target, thus affording a higher saturation with the drug being targeted in this invention.

In preferred embodiments, the constructs are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W.B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

DNL (Dock and Lock) Technology

The DNL method is based on the specific protein/protein interactions between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell. Biol. 2004; 5: 959). PKA, which plays a central role in the signal transduction pathway triggered by the binding of cAMP to the R subunits of PKA, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265:21561).

Since the first AKAP, microtubule-associated protein-2, was characterized in 1984 (Lohmann et al., Proc. Natl. Acad. Sci. USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell. Biol. 2004; 5:959). The AD of AKAPs for PKA is an amphipathic helix of 14-18 residues (Carr et al., J. Biol. Chem. 1991; 266:14188) and any such known AD sequence may be utilized to form a DNL complex. The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). Interestingly, AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

DDD of Human RIIα and AD of AKAPs as Linker Modules

We have developed a platform technology to utilize the DDD of human RIIα and the AD of AKAPs as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions bring the reactive thiol groups placed onto both the DDD and AD into proximity (Chimura et al., Proc. Natl. Acad. Sci. USA. 2001; 98:8480) to ligate site-specifically.

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, nucleic acids, cytokines and PEG.

DDD and AD Sequence Variants

In certain embodiments, the AD and DDD sequences incorporated into the DNL complex comprise the amino acid sequences of DDD1 (SEQ ID NO:1) and AD1 (SEQ ID NO:3) below. In more preferred embodiments, the AD and DDD sequences comprise the amino acid sequences of DDD2 (SEQ ID NO:2) and AD2 (SEQ ID NO:4), which are designed to promote disulfide bond formation between the DDD and AD moieties.

```
DDD1                                    (SEQ ID NO: 1)
SHIQIPPGLTELLQGYTVEVLRQQPPDLVEFAVEYFTRLREARA

DDD2                                    (SEQ ID NO: 2)
CGHIQIPPGLTELLQGYTVEVLRQQPPDLVEFAVEYFTRLREARA

AD1                                     (SEQ ID NO: 3)
QIEYLAKQIVDNAIQQA

AD2                                     (SEQ ID NO: 4)
CGQIFYLAKQIVDNAIQQAGC
```

However, in alternative embodiments sequence variants AD and/or DDD moieties may be utilized in construction of the DNL complexes. The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400:493-99; Gold et al., 2006, Mol Cell 24:383-95; Kinderman et al., 2006, Mol Cell 24:397-408, the entire text of each of which is incorporated herein by reference.)

For example, Kinderman et al. (2006) examined the crystal structure of the AD-DDD binding interaction and concluded that the human DDD sequence contained a number of conserved amino acid residues that were important in either dimer formation or AKAP binding, underlined below in SEQ ID NO:1. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding. Thus, a potential alternative DDD sequence of use for construction of DNL complexes is shown in SEQ ID NO:5, wherein "X" represents a conservative amino acid substitution. Conservative amino acid substitutions are discussed in more detail below, but could involve for example substitution of an aspartate residue for a glutamate residue, or a leucine or valine residue for an isoleucine residue, etc. Such conservative amino acid substitutions are well known in the art.

```
Human DDD sequence from protein kinase A
                                              (SEQ ID NO: 1)
SHIQIPPGLTELLQGYTVEVLRQQPPDLVEFAVEYFTRLREARA (SEQ ID NO: 5)
XXIXIXXXLXXLLXXYXVXVLXXXXXXLVXFXVXYFXXLXXXXX
```

Alto et al. (2003) performed a bioinformatic analysis of the AD sequence of various AKAP proteins to design an RII selective AD sequence called AKAP-IS (SEQ ID NO:3), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:3. Therefore, the skilled artisan will realize that variants which may function for DNL constructs are indicated by SEQ ID NO:6, where "X" is a conservative amino acid substitution.

```
AKAP-IS sequence
                                              (SEQ ID NO: 3)
QIEYLAKQIVDNAIQQA (SEQ ID NO: 6)
XXXXXAXXIVXXAIXXX
```

Similarly, Gold (2006) utilized crystallography and peptide screening to develop a SuperAKAP-IS sequence (SEQ ID NO:7), exhibiting a five order of magnitude higher selectivity for the RII isoform of PKA compared with the RI isoform. Underlined residues indicate the positions of amino acid substitutions, relative to the AKAP-IS sequence, that increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL constructs. Other alternative sequences that might be substituted for the AKAP-IS AD sequence are shown in SEQ ID NO:8-10. Substitutions relative to the AKAP-IS sequence are underlined. It is anticipated that, as with the AKAP-IS sequence shown in SEQ ID NO:3, the AD moiety may also include the additional N-terminal residues cysteine and glycine and C-terminal residues glycine and cysteine, as shown in SEQ ID NO:4.

```
SuperAKAP-IS                                  (SEQ ID NO: 7)
QIEYVAKQIVDYAIHQA Alternative AKAP sequences
                                              (SEQ ID NO: 8)
QIEYKAKQIVDHAIHQA (SEQ ID NO: 9)
QIEYHAKQIVDHAIHQA (SEQ ID NO: 10)
QIEYVAKQIVDHAIHQA
```

Stokka et al. (2006) also developed peptide competitors of AKAP binding to PKA, shown in SEQ ID NO:11-13. The peptide antagonists were designated as Ht31 (SEQ ID NO:11), RIAD (SEQ ID NO:12) and PV-38 (SEQ ID NO:13). The Ht-31 peptide exhibited a greater affinity for the RII isoform of PKA, while the RIAD and PV-38 showed higher affinity for RI.

```
Ht31                                          (SEQ ID NO: 11)
DLIFEAASRIVDAVIEQVKAAGAY

RIAD                                          (SEQ ID NO: 12)
LEQYANQLADQIIKEATE

PV-38                                         (SEQ ID NO: 13)
FEELAWKIAKMIWSDVFQQC
```

Hundsrucker et al. (2006) developed still other peptide competitors for AKAP binding to PKA, with a binding constant as low as 0.4 nM to the DDD of the RII form of PKA. The sequences of various AKAP antagonistic peptides is provided in Table 1 of Hundsrucker et al. (incorporated herein by reference). Residues that were highly conserved among the AD domains of different AKAP proteins are indicated below by underlining with reference to the AKAP IS sequence (SEQ ID NO:3). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence are shown in SEQ ID NO:14-16.

```
AKAP-IS                                       (SEQ ID NO: 3)
QIEYLAKQIVDNAIQQA

AKAP7δ-wt-pep                                 (SEQ ID NO: 14)
PEDAELVRLSKRLVENAVLKAVQQY AKAP7δ-L304T-pep                              (SEQ ID NO: 15)
PEDAELVRTSKRLVENAVLKAVQQY AKAP7δ-L308D-pep                              (SEQ ID NO: 16)
PEDAELVRLSKRDVENAVLKAVQQY
```

Carr et al. (2001) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:1. Residues that were particularly conserved are further indicated by italics. The residues overlap with, but are not identical to those suggested by Kinderman et al. (2006) to be important for binding to AKAP proteins. Thus, a potential DDD sequence is indicated in SEQ ID NO:17, wherein "X" represents a conservative amino acid substitution.

```
                                                 (SEQ ID NO: 1)
SHIQIPPGLTELLQGYTVEVLRQQPPDLVEFAVEYFTRLREARA (SEQ ID NO: 17)
XHIXIPXGLXELLQGYTXEVLRXQPXDLVEFAXXYFXXLXEXRX
```

The skilled artisan will realize that in general, those amino acid residues that are highly conserved in the DDD and AD sequences from different proteins are ones that it may be preferred to remain constant in making amino acid substitutions, while residues that are less highly conserved may be more easily varied to produce sequence variants of the AD and/or DDD sequences described herein.

In addition to sequence variants of the DDD and/or AD moieties, in certain embodiments it may be preferred to introduce sequence variations in the antibody moiety or the linker peptide sequence joining the antibody with the AD sequence. In one illustrative example, three possible variants of fusion protein sequences, are shown in SEQ ID NO:18-20.

```
(L)                         (SEQ ID NO: 18)
QKSLSLSPGLGSGGGSGGCG (A)                         (SEQ ID NO: 19)
QKSLSLSPGAGSGGGSGGCG (-)                         (SEQ ID NO: 20)
QKSLSLSPGGSGGGSGGCG
```

Production of Antibody Fragments

Methods of monoclonal antibody production are well known in the art and any such known method may be used to produce antibodies of use in the claimed methods and compositions. Some embodiments may concern antibody fragments. Such antibody fragments may be obtained by pepsin or papain digestion of whole antibodies by conventional methods. For example, antibody fragments may be produced by enzymatic cleavage of antibodies with pepsin to provide a 5S fragment denoted F(ab')$_2$. This fragment may be further cleaved using a thiol reducing agent and, optionally, a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment. Exemplary methods for producing antibody fragments are disclosed in U.S. Pat. No. 4,036,945; U.S. Pat. No. 4,331,647; Nisonoff et al., 1960, Arch. Biochem. Biophys., 89:230; Porter, 1959, Biochem. J., 73:119; Edelman et al., 1967, METHODS IN ENZYMOLOGY, page 422 (Academic Press), and Coligan et al. (eds.), 1991, CURRENT PROTOCOLS IN IMMUNOLOGY, (John Wiley & Sons).

Other methods of cleaving antibodies, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., 1972, Proc. Nat'l. Acad. Sci. USA, 69:2659. Alternatively, the variable chains may be linked by an intermolecular disulfide bond or cross-linked by chemicals such as glutaraldehyde. See Sandhu, 1992, Crit. Rev. Biotech., 12:437.

Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains, connected by an oligonucleotide linker sequence. Methods for producing sFvs are well-known in the art. See Whitlow et al., 1991, Methods: A Companion to Methods in Enzymology 2:97; Bird et al., 1988, Science, 242:423; U.S. Pat. No. 4,946,778; Pack et al., 1993, Bio/Technology, 11:1271, and Sandhu, 1992, Crit. Rev. Biotech., 12:437.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, Methods: A Companion to Methods in Enzymology 2:106; Ritter et al. (eds.), 1995, MONOCLONAL ANTIBODIES: PRODUCTION, ENGINEERING AND CLINICAL APPLICATION, pages 166-179 (Cambridge University Press); Birch et al., (eds.), 1995, MONOCLONAL ANTIBODIES: PRINCIPLES AND APPLICATIONS, pages 137-185 (Wiley-Liss, Inc.)

Chimeric and Humanized Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. The affinity of humanized antibodies for a target may also be increased by selected modification of the CDR sequences (WO0029584A1). Techniques for production of humanized monoclonal antibodies are well known in the art. (See, e.g., Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immun., 1993, 150:2844.)

Other embodiments may concern non-human primate antibodies. General techniques for raising therapeutically useful antibodies in baboons may be found, for example, in Goldenberg et al., WO 91/11465 (1991), and in Losman et al., Int. J. Cancer 46: 310 (1990). In another embodiment, an antibody may be a human monoclonal antibody. Such antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994).

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens. In one non-limiting example of this methodology, Dantas-Barbosa et al. (2005) constructed a phage display library of human Fab antibody fragments from osteosarcoma patients. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Such human antibodies may be coupled to other molecules by chemical cross-linking or other known methodologies. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Avimers

In certain embodiments, the precursors, monomers and/or complexes described herein may comprise one or more avimer sequences. Avimers are a class of binding proteins somewhat similar to antibodies in their affinities and specifities for various target molecules. They were developed from human extracellular receptor domains by in vitro exon shuffling and phage display. (Silverman et al., 2005, Nat. Biotechnol. 23:1493-94; Silverman et al., 2006, Nat. Biotechnol. 24:220.) The resulting multidomain proteins may comprise multiple independent binding domains, that may exhibit improved affinity (in some cases sub-nanomolar) and specificity compared with single-epitope binding proteins. (Id.) In various embodiments, avimers may be attached to, for example, DDD sequences for use in the claimed methods and compositions. Additional details concerning methods of construction and use of avimers are disclosed, for example, in U.S. Patent Application Publication Nos. 20040175756, 20050048512, 20050053973, 20050089932 and 20050221384, the Examples section of each of which is incorporated herein by reference.

Phage Display

Certain embodiments of the claimed compositions and/or methods may concern binding peptides and/or peptide mimetics of various target molecules, cells or tissues. Binding peptides may be identified by any method known in the art, including but not limiting to the phage display technique. Various methods of phage display and techniques for producing diverse populations of peptides are well known in the art. For example, U.S. Pat. Nos. 5,223,409; 5,622,699 and 6,068,829, each of which is incorporated herein by reference, disclose methods for preparing a phage library. The phage display technique involves genetically manipulating bacteriophage so that small peptides can be expressed on their surface (Smith and Scott, 1985, Science 228:1315-1317; Smith and Scott, 1993, Meth. Enzymol. 21:228-257).

Targeting amino acid sequences selective for a given organ, tissue, cell type or target molecule may be isolated by panning (Pasqualini and Ruoslahti, 1996, Nature 380:364-366; Pasqualini, 1999, The Quart. J. Nucl. Med. 43:159-162). In brief, a library of phage containing putative targeting peptides is administered to an intact organism or to isolated organs, tissues, cell types or target molecules and samples containing bound phage are collected. Phage that bind to a target may be eluted from a target organ, tissue, cell type or target molecule and then amplified by growing them in host bacteria.

Multiple rounds of panning may be performed until a population of selective or specific binders is obtained. The amino acid sequence of the peptides may be determined by sequencing the DNA corresponding to the targeting peptide insert in the phage genome. The identified targeting peptide may then be produced as a synthetic peptide by standard protein chemistry techniques (Arap et al., 1998a, Smith et al., 1985).

Aptamers

In certain embodiments, a targeting moiety of use may be an aptamer. Methods of constructing and determining the binding characteristics of aptamers are well known in the art. For example, such techniques are described in U.S. Pat. Nos. 5,582,981, 5,595,877 and 5,637,459, each incorporated herein by reference. Methods for preparation and screening of aptamers that bind to particular targets of interest are well known, for example U.S. Pat. Nos. 5,475,096 and 5,270,163, each incorporated by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers need to contain the sequence that confers binding specificity, but may be extended with flanking regions and otherwise derivatized. In preferred embodiments, the binding sequences of aptamers may be flanked by primer-binding sequences, facilitating the amplification of the aptamers by PCR or other amplification techniques.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)NR$_2$, P(O)R, P(O)OR', CO, or CNR$_2$, wherein R is H or alkyl (1-20C) and R' is alkyl (1-20C); in addition, this group may be attached to adjacent nucleotides through O or S. Not all linkages in an oligomer need to be identical.

Conjugation Protocols

The preferred conjugation protocol is based on an alkyne-azide (preferably monosubstituted acetylene-azide), a thiol-maleimide, a thiol-vinylsulfone, a thiol-bromoacetamide, or a thiol-iodoacetamide reaction that are facile at neutral or slightly acidic pH.

Suitable routes of administration of the conjugates of the preferred embodiments of the present invention include, without limitation, oral, parenteral, rectal, transmucosal, intestinal administration, intramuscular, subcutaneous, intramedullary, intrathecal, direct intraventricular, intravenous, intravitreal, intraperitoneal, intranasal, or intraocular injections. The preferred routes of administration are parenteral. Alternatively, one may administer the compound in a local rather than systemic manner, for example, via injection of the compound directly into a solid tumor.

Kits

Various embodiments may concern kits containing components suitable for treating diseased tissue in a patient. Exemplary kits may contain at least one or more constructs as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used. In certain embodiments, a therapeutic agent may be provided in the form of a prefilled syringe or autoinjection pen containing a sterile, liquid formulation or lyophilized preparation.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

The invention is illustrated with examples below without limiting the scope thereof.

Example 1

Introduction of COOH Groups on Dextran

Dextran (70 kD MW) was derivatized with 5-bromohexanoic acid and 4 M sodium hydroxide at 80° C. for 3 h. The material was then acidified to pH ~4, optionally extracted with an organic solvent to remove unreacted bromohexanoic acid, and dialyzed, in a 10 kD molecular weight cut-off (MWCO) dialysis cassette, against water with 3 water changes. The aqueous product was lyophilized. A known amount of modified dextran was titrated against 0.1 N sodium hydroxide to estimate the number of carboxylic acid groups introduced. This showed that 44-to-100 COOH groups were introduced per dextran, corresponding to 11% to 25% of monomeric units modified.

Example 2

Derivatization of COOH-Appended Dextran (70 kD MW)

The product of Example 1, with 44 COOH/70 kD dextran, was treated with water soluble carbodiimide, EDC, and BOC-hydrazine, each at an equivalent corresponding to ~50% of the COOH content. Briefly, EDC treatment was done at an acidic pH of ~6, and then the monoprotected hydrazine was added and the pH was raised to 7.4. After incubation for 2 to 3 h at the room temperature, the product was purified by ultrafiltration using centrifugal filter with a 30 K MWCO. The recovered product was determined, by titration against 0.1 N sodium hydroxide, to contain 24 COOH/70 kD dextran. This indicated derivatization of 20 COOH moieties as BOC hydrazide. The process was repeated with further derivatization using EDC and ethylene diamine such that the new intermediate now had 8 amino groups, 20 BOC hydrazide and 16 COOH per dextran. Finally, optimization was carried out for introducing ~1 reactive moiety per dextran polymer. This was done by reacting amine, BOC-hydrazide and COOH-containing dextran with varying molar equivalents of SPDP (N-succinimidyl-3-(2-PyridylDithio)-Proprionate), and analyzing the number of activated disulfide groups so introduced by spectrophotometrically assaying for 2 thiopyridone, at 343 nm, liberated by reaction with dithiothreitol. This analysis showed that a 1:1 level of activated disulfide-to-dextran substitution was obtained when using a 5.3-fold molar excess of SPDP reagent.

Example 3

Sequential Derivatization of COOH-Appended Dextran (40 kD MW) to a Doxorubicin-Substituted Polymer Dextran (40 kD) was derivatized with bromohexanoic acid and sodium hydroxide, as in Example 1, to possess ~60 COOH per dextran; this was derivatized with BOC hydrazine and EDC to ~50% level of COOH content, which was ~30

Boc-hydrazide groups. Deprotection was carried out with 3M hydrochloric acid, and the product was purified by ultrafiltration. Conjugation with doxorubicin was examined under conditions of pH 5 and pH 6. This showed that aqueous condition derivatization was more efficient at pH 5, with the introduction of 20 Dox groups versus 12 Dox introduced at pH 6. Doxorubicin content was determined from absorbance at 496 nm and correlation with a doxorubicin standard curve.

Example 4

Sequential Derivatization of COOH-Appended Dextran (40 kD MW) to a Doxorubicin-Substituted Polymer by the 'Click Chemistry' Approach Carboxyl-derivatized dextran (40 kD; ~60 COOH) from Example 3 (0.0047 mmol of dextran; 0.282 mmol w.r.t. COOH) was reacted with 2.6 mmol of EDC and 2.1 mmol of propargylamine. The product, acetylene-added dextran, was purified by repeated ultrafiltration-diafiltration. The acetylene content was estimated to be 50-to-60 per 40 kd MW dextran, based on back-titration of the underivatized carboxylic acid groups.

The azide-incorporated doxorubicin hydrazone was prepared from doxorubicin (0.44 mmol) and 6-azidohexanoic acid hydrazide (as TFA salt; 1.5 mmol) in methanol at room temperature overnight. The solvent was evaporated off, and the excess hydrazide reagent was removed by trituration with acetonitrile. The solid product so obtained had a retention time of 9.92 min when analyzed on a reverse phase HPLC column using gradient elution (100% A going to 100% B in 10 min at a flow of 3 mL/min, and maintaining at 100% B for the next 5 min; A=0.3% ammonium acetate pH 4.43; B=90% acetonitrile, 10% A; in-line absorbance detection at 254 nm), and was 75% pure, with the remaining material mostly composed of unreacted doxorubicin. The product showed, in electrospray mass spectrum, peaks at m/e 696 (M−H), and m/e 732 (M+Cl), indicating the identity of the product. [The hydrazide reagent used herein was prepared in 3 steps from 6-bromohexanoic acid (2 g) by first reacting with sodium azide (1 g) in DMSO at 50° C. for 2 hr followed by extractive work up with water and ethylacetate. The ethylacetate extract was washed sequentially with 1N HCl solution and brine and dried. The product after solvent removal was re-dissolved in dichloromethane (50 mL) and reacted with 2 g of EDC (10 mmol) and 1.4 g (10 mmol) of BOC-hydrazide for 1 hour at ambient temperature. Extractive work up with 1N HCl, satd. $NaHCO_3$, and brine, followed by drying and solvent removal furnished the required product which was subjected to TFA-mediated BOC deprotection using 10 mL of 1:1 TFA-$CH_2Cl_2$. This material was used for derivatizing doxorubicin.]

This partially-purified material was used as such for coupling to acetylene-containing dextran as follows. Acetylene-added dextran (0.1 mL of 3.35 mM) was reacted with 2 mg (1.44 μmol; 57-fold molar excess w.r.t to dextran) of doxorubicin-azide, incorporating an acid-cleavable hydrazone, 0.05 molar equiv of cupric sulfate (w.r.t. doxorubicin azide), and 0.5 molar equiv of sodium ascorbate (w.r.t. doxorubicin azide), and stirred overnight at ambient temperature. Reaction pH was maintained at ~6.7. The product was purified by 3 successive UF-DF using 10K MWCO centrifugal filter. The product was lyophilized to obtain 13.5 mg of doxorubicin-derivatized dextran. The doxorubicin substitution was determined to be 8.2 per dextran.

Scheme-2 describes the reactions.

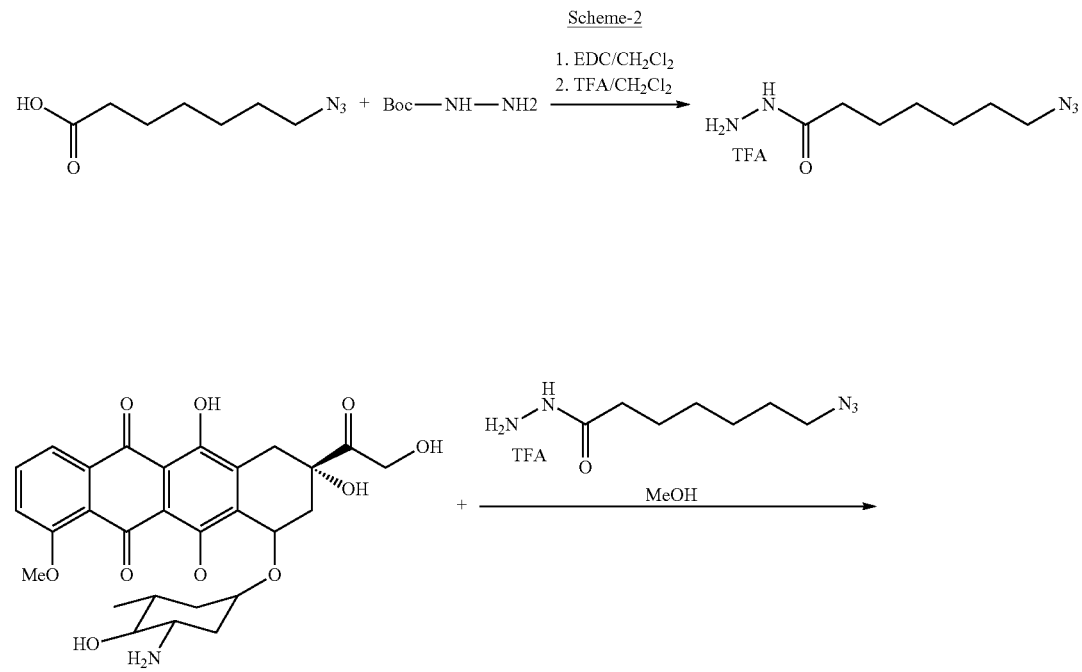

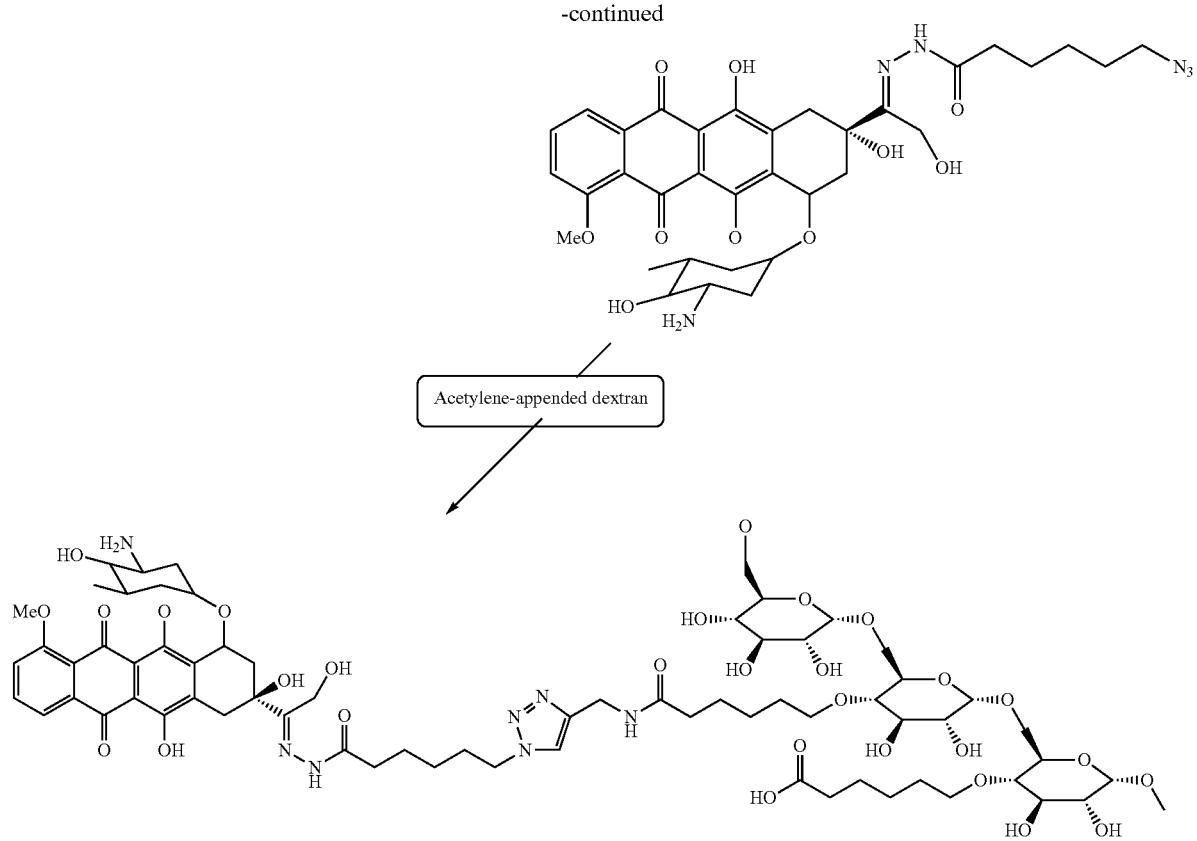

Example 5

Preparation of SN38-20-O-glycinato-PEG-azide 0.5 g (0.9 mmol) of commercially available O-(2-Azido-ethyl)-O'—(N-diglycolyl-2-aminoethyl)heptaethylenegly-col was activated with 1.2 equiv. of DCC (0.186 g) and 1.2 equiv. of N-hydroxysuccinimide (0.103 g) and catalytic amount of DMAP (0.003 g) in dichloromethane (10 mL) for 30 min at ambient temperature. To this was added a solution of 0.42 g (0.76 mmol) of SN38-20-O-glycinate, in 10 mL dichloromethane, and DIEA (0.145 mL, 1.1 equiv.) After stirring for 30 min, the product was purified by flash chromatography on silica gel (230-400 mesh) using $CH_2Cl_2$-MeOH gradient elution. The oily product (0.74 g, 98% yield) had HPLC retention time of 9.86 min under the HPLC conditions described in Example 4. The product was characterized by electrospray mass spectrum. M+H at m/e 986, M+Na at m/e 1008; in the negative ion mode, M–H at m/e 985. Calculated for $C_{45}H_{64}N_7O_{17}$ (M+H): 986.4360; found: 986.4361.

Scheme-3 shows the synthesis.

Scheme-3

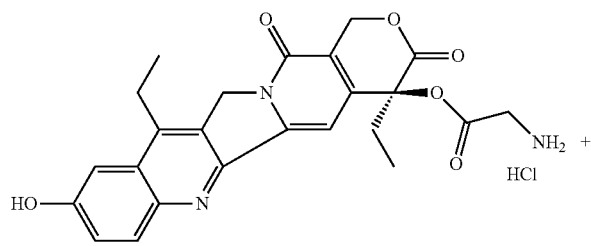

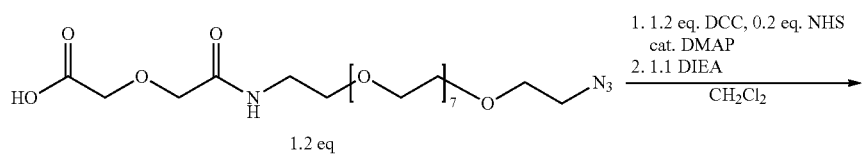

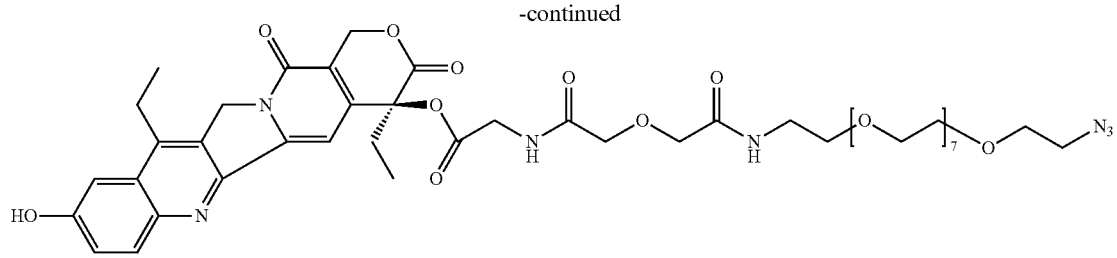

Example 6

Preparation of N₃-PEG-Phe-Lys(MMT)-PABOCO-20-O—SN38-10-O—BOC 0.527 g (0.95 mmol) of O-(2-Azidoethyl)-O'—(N-diglycolyl-2-aminoethyl)pheptaethyleneglycol was activated with 1.1 equiv. of DCC (0.182 g) and 1.2 equiv. of N-hydroxysuccinimide (0.119 g) and catalytic amount of DMAP (0.005 g) in dichloromethane (20 mL) for 30 min at ambient temperature. To this mixture was added the known Phe-Lys(MMT)-PABOH (0.58 g; 0.865 mmol), where MMT stands for monomethoxytrityl and PABOH is p-aminobenzyl alcohol moieties, and DIEA (0.158 mL; 1.5 equiv). Stirred for 1 hr more, and the product was purified by flash chromatography. Yield: 84%. Mass spectrum: M+H: m/e 1207. This material was coupled to 1 equivalent of BOC—SN38-20-O-chloroformate. [The latter was prepared from BOC—SN38, triphosgene (0.4 equiv.) and DMAP (3.2 equiv) in dichloromethane, and as such without purification.]. The title product was obtained in 60-80% yield after purification by flash chromatography. M+H: Calculated 1725.7981; found: 1725.7953.

Scheme-4 shows the preparation.

Scheme-4

Step-1

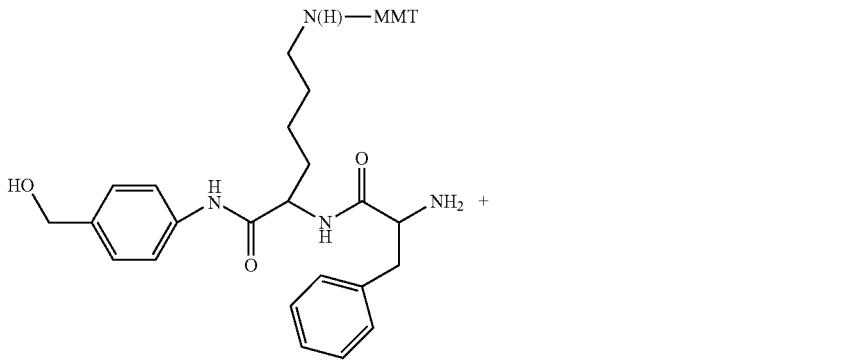

MMT = momomethoxytrityl

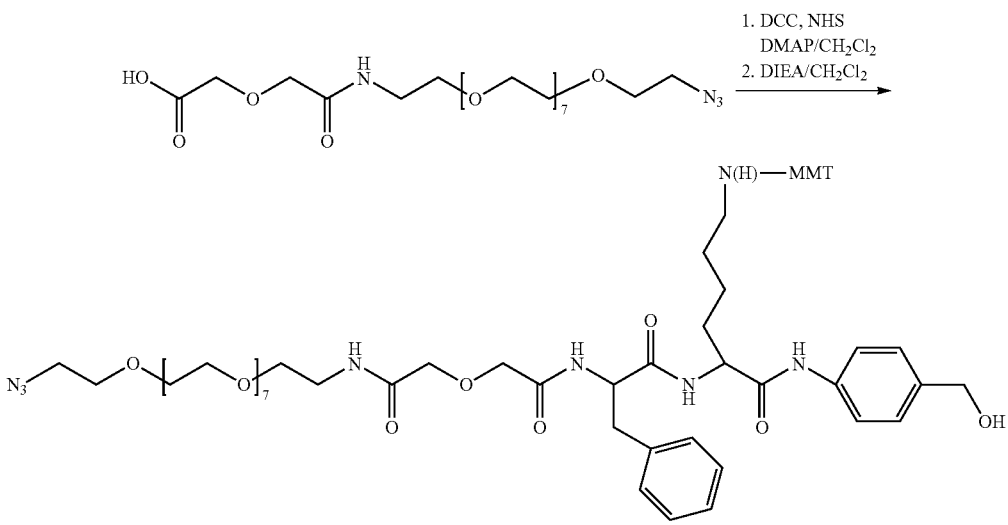

Azido-PEG-Phe-Lys(MMT)-PABOH

Step-2

-continued

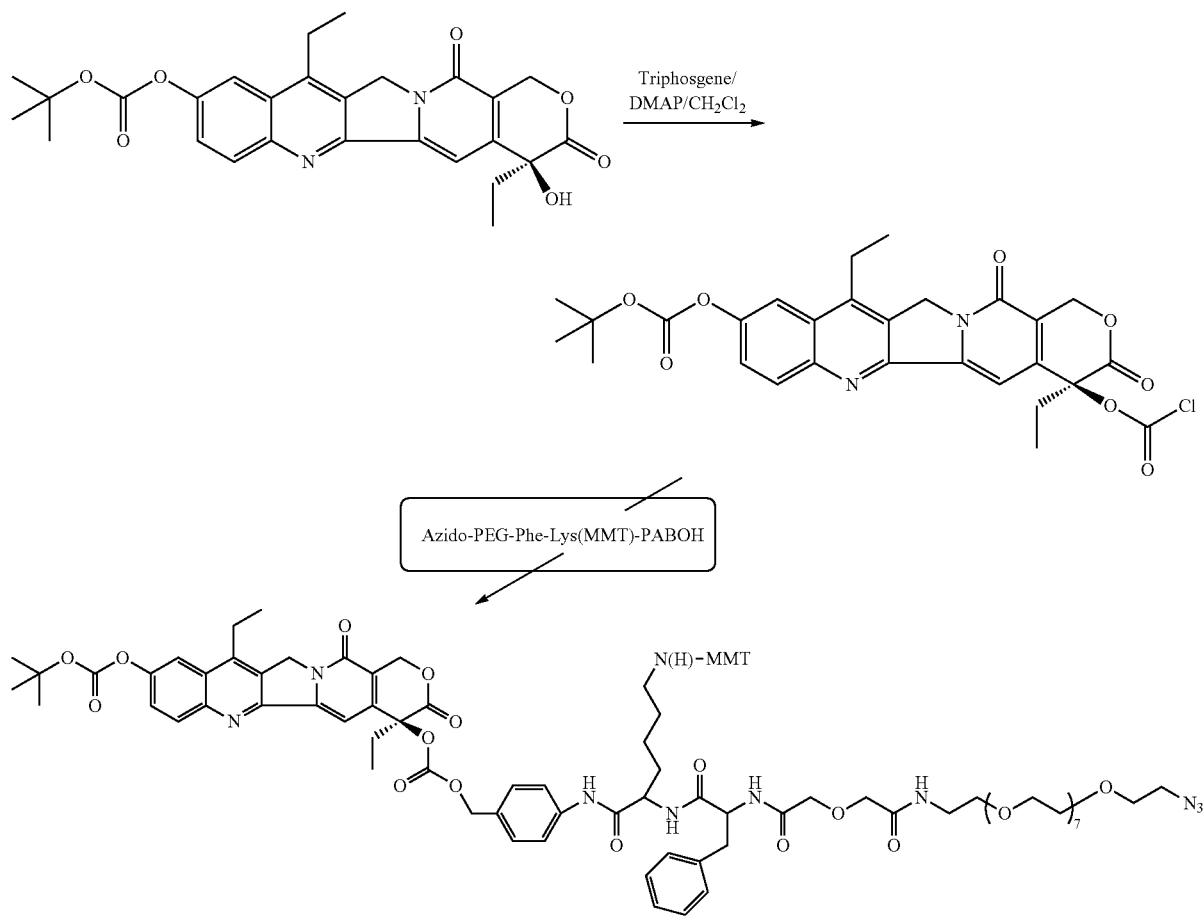

Example 7

Preparation of azido-PEG-Phe-Lys(MMT)-PABOCO-20-O-glycinato SN38

The intermediate azido-PEG-Phe-Lys(MMT)-PABOH (0.27 g; 0.22 mmol) from Example 10 was activated with bis(nitrophenyl)carbonate (0.204 g; 3 equiv.) and DIEA (1 equiv.) in dichloromethane (10 mL) for 3 days at ambient temperature. Flash chromatography furnished the pure activated product (yield: 69%), M+H Calc for $C_{71}H_{90}N_9O_{19}$: 1372.6347; found: 1372.6347. Activated carbonate product (0.08 g; 0.058 mmol) was coupled to SN38-20-O-glycinate (0.028 g; 0.058 mmol) in DMF (1 mL) and DIEA (0.025 mL; 2.5 equiv.). After 4 h of stirring, solvent was removed and the crude product was purified by flash chromatography. Yield: 0.052 g (54%). M+H Calc for $C_{89}H_{108}N_{11}O_{22}$: 1682.7665; found: 1682.7682.

Scheme-5 describes the reactions.

Scheme-5

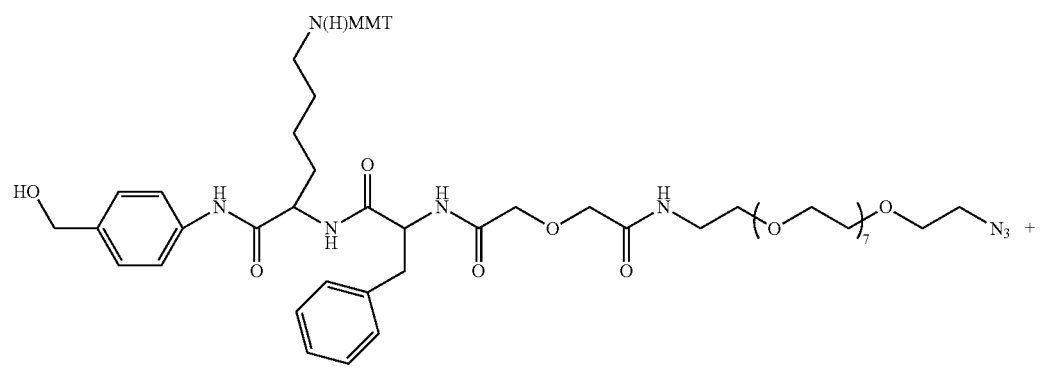

MMT = monomethoxytrityl

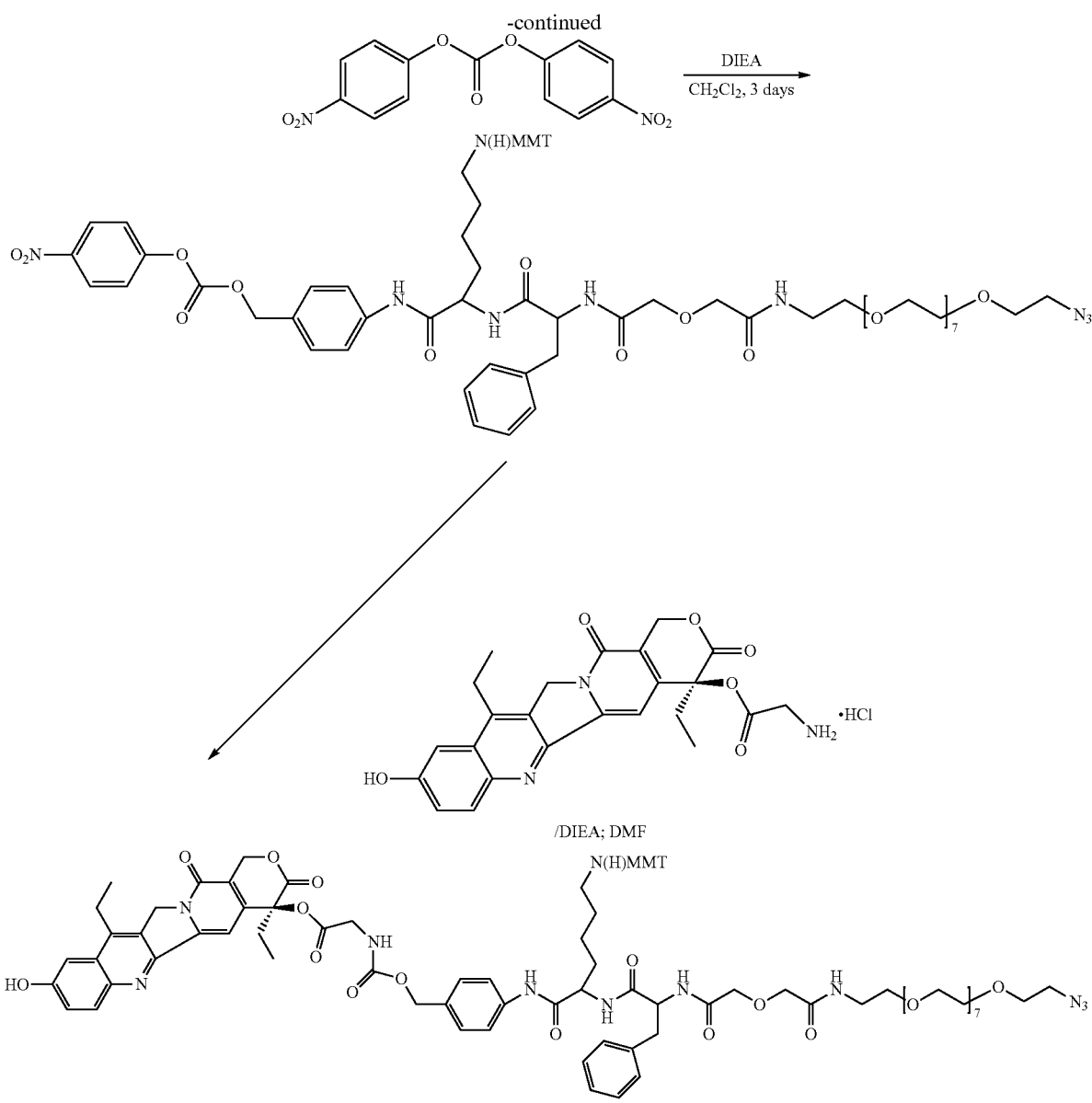

Example 8

Derivatization of Succinimidyl 4-Maleimidomethyl-Cyclohexane Carboxylate (SMCC) with N—BOC-2,2'-(Ethylenedioxy)Diethylamine, Followed by BOC-Deprotection SMCC (0.334 g), monoprotected diamine reagent (0.248 g) and DIEA (0.17 mL) were dissolved in dichloromethane (20 mL), stirred at ambient temperature for 20 min. The product was purified by flash chromatography, and further reacted with TFA (2 mL) and anisole (0.5 mL) for 2 hours, and the final product was isolated after removal of TFA and anisole. The corresponding hydrochloride salt was prepared by dissolving in HCl and evaporating off HCl. Mass spectrum: M+H m/e 368. The process schematically shown in Scheme-6.

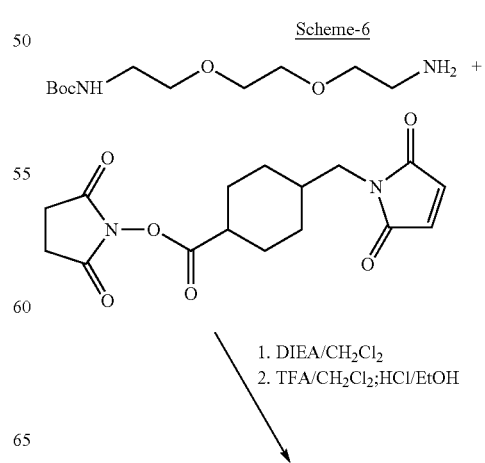

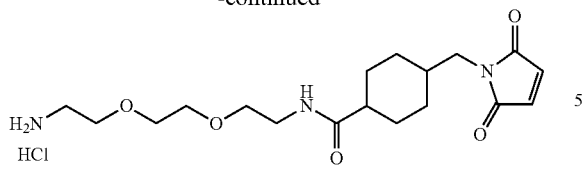

Example 9

Derivatization of Acetylene-Containing Dextran of Example-4 with the Product of Example 8

To an aqueous solution of acetylene-dextran (40 KD MW; 0.425 g) in 10 mL of water, added product of example 8 (0.085 g; 20 equiv. w.r.t dextran) and EDC (0.0406 g; 20 equiv.), stirred for 1 hour. Purified by ultrafiltration-diafiltration using 10 kd MW CO filter. Anthrone assay for dextran showed the dextran concentration to be 28.6 mg/mL. Reverese Ellman's assay using excess of 2-mercaptoethanol and determining the excess unsused 2-ME by Ellman's assay gave a value of 5.4 maleimides substituted on to dextran. Scheme-7 depicts the reactions.

Scheme-7

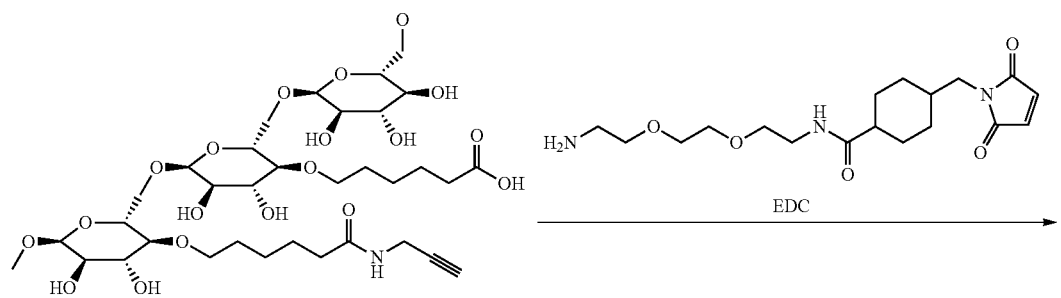

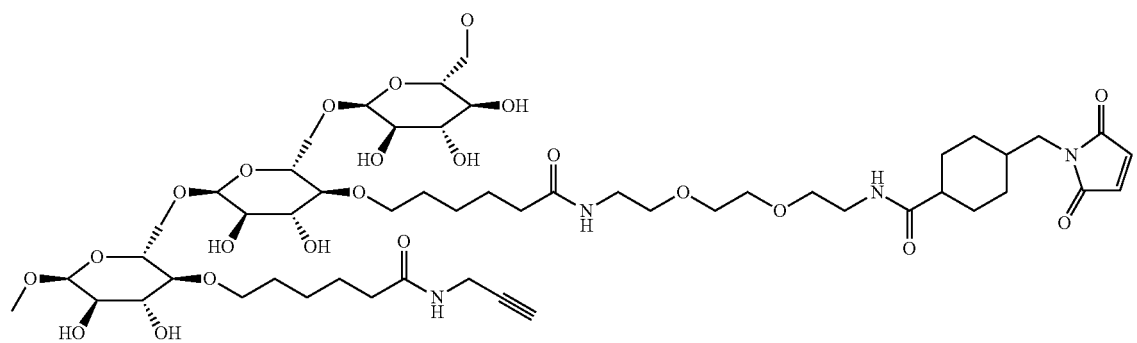

Example 10

Click Chemistry Coupling of Dextran-Acetylene$_{(50-60)}$-maleimide$_{(5,5)}$ with SN38-20-O-Glycinato-PEG-Azide Products of Example 5 or Example 6 or Example 7

10 mL of 28.6 mg/mL solution of the dextran derivative of Example 9 was reacted with 0.42 M DMSO solution of the SN38 derivative specified in Example 5 (70 equiv.) in the presence of a catalytic amount of cupric sulfate and sodium ascorbate in a 10-fold excess over copper sulfate. DMSO concentration was 20% v/v. The somewhat cloudy solution was stirred for 4 hr. The product was purified by ultrafiltration/diafiltration, using 0.2 M aqueous EDTA, followed by gel filtration. The product was characterized by anthrone assay (10.74 mg/mL), and SN38 concentration was determined by absorbance at 366 nm and correlation with a standard curve. SN38 molar substitution was calculated to be 36.6. Free unremoved SN38 level was estimated to be 5% by HPLC. The product of reaction using azide-SN38 of Example 5 is illustrated below in Scheme-8.

Scheme-8

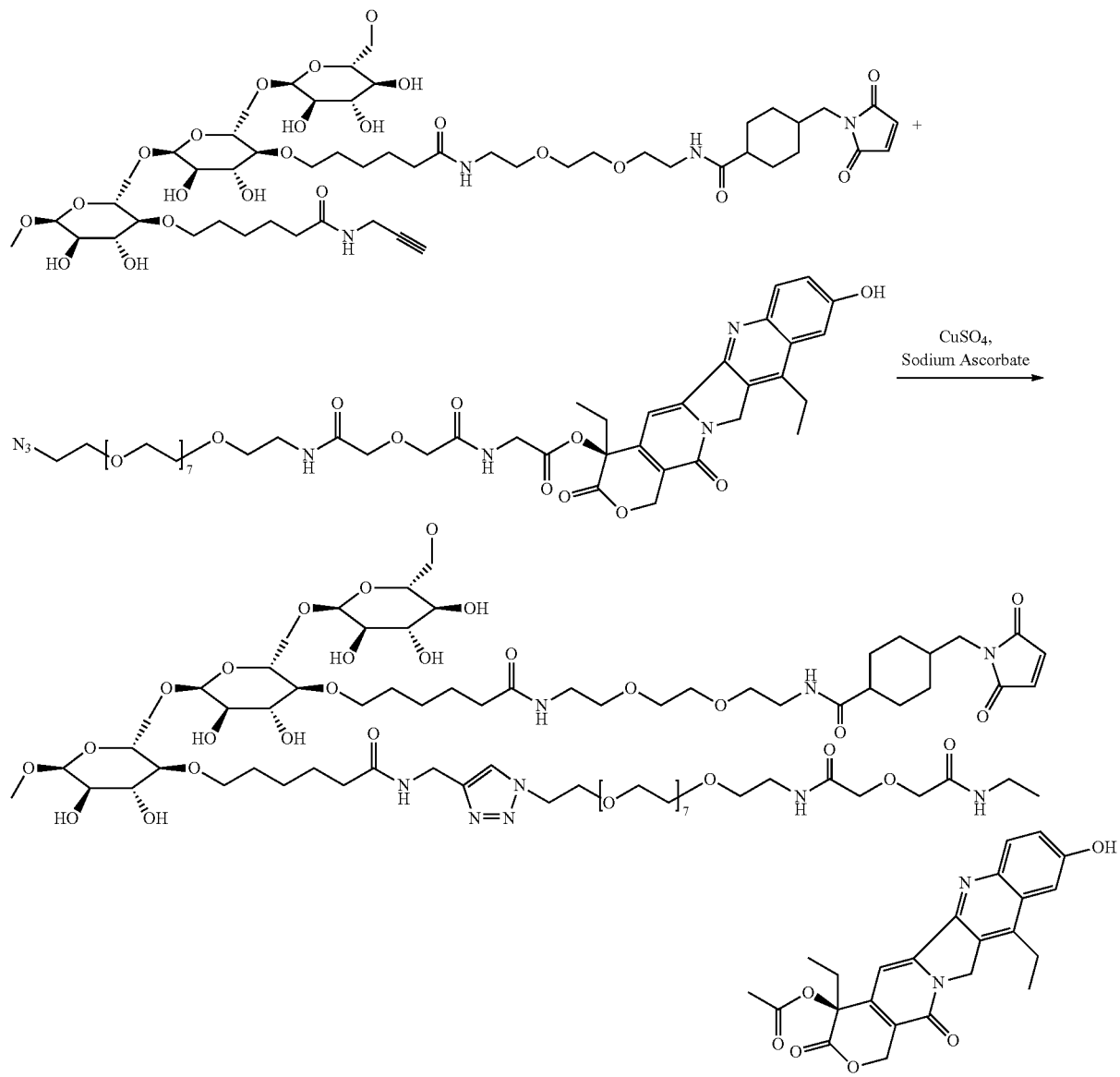

In a similar fashion, the dextran derivative of Example 9 is reacted with the azido-SN38 derivative of Examples 6 or 7 to obtain the corresponding dextran conjugates. In these cases, the BOC and MMT protecting groups are subsequently removed by treatment with 2 N hydrochloric acid or by a short-duration treatment (<5 min) with trifluoroacetic acid. Alternatively, the protecting groups are removed first, followed by click chemistry coupling to the dextran derivative of Example 9.

Example 11

Coupling of any Dextran Derivative of Example 10 with a Thiol-Containing Material Incorporating a Recognition Moiety The reaction is done by coupling a maleimide-appended dextran of Example 10 with 5.4 equivalent of the recognition moiety-incorporated, thiol-containing peptide in 75 mM sodium acetate-1 mM EDTA, pH 6.5, for 1 hr. For pretargeting, prototypical peptide in this regard is Ac-Cys-(AA)$_n$-Lys (HSG)-NH$_2$, wherein AA is an amino acid, and n is an integer from 1-20, preferably 1-3. One of the amino acids represented by 'AA' can be lysine with HSG substituted on the lysine side chain amino group, thereby making the peptide a bis-HSG-containing peptide. The substitution of the N-terminal cysteine can be a chelator such as benzyl-DTPA, instead of acyl, for determining by metal-binding assays the number of peptides attached to the polymer. For DNL coupling, the peptide is cysteine-containing anchoring domain ('AD') peptide, such as illustrated in paragraph 0051. The other recognition moieties described in paragraph 0014 are also useful in this reaction after suitable prior derivatization of the same to possess a thiol group. The product is purified by ultrafiltration-diafiltration, followed by centrifuged size-exclusion column chromatography using non-EDTA buffer. Using an HSG-incorporated peptide, which further contains a metal chelator, metal-binding assay gives a chelator content of 2.5 per dextran. This suggests that at least 2.5 mole per mole of dextran is accessible for reaction with thiol-containing material. A test labeling with In-111 acetate is done, and the material is purified by size-exclusion chromatography. HPLC analysis of the radiolabeled material as well as that of the material complexed with anti-HSG antibody (murine 679) shows complete complexation, as revealed by the shift of the SE HPLC peak due to In-111-dextran to a peak due to the higher MW of the dextran: 679 antibody complex. The unlabeled material is also shown to be complexed with murine 679 antibody, as the broad size-exclusion HPLC peak due to dextran derivative is shifted to a relatively sharper and faster eluting peak, indicating complexation with murine 679 antibody. The conjugation to HSG-containing peptide is given in Scheme-9.

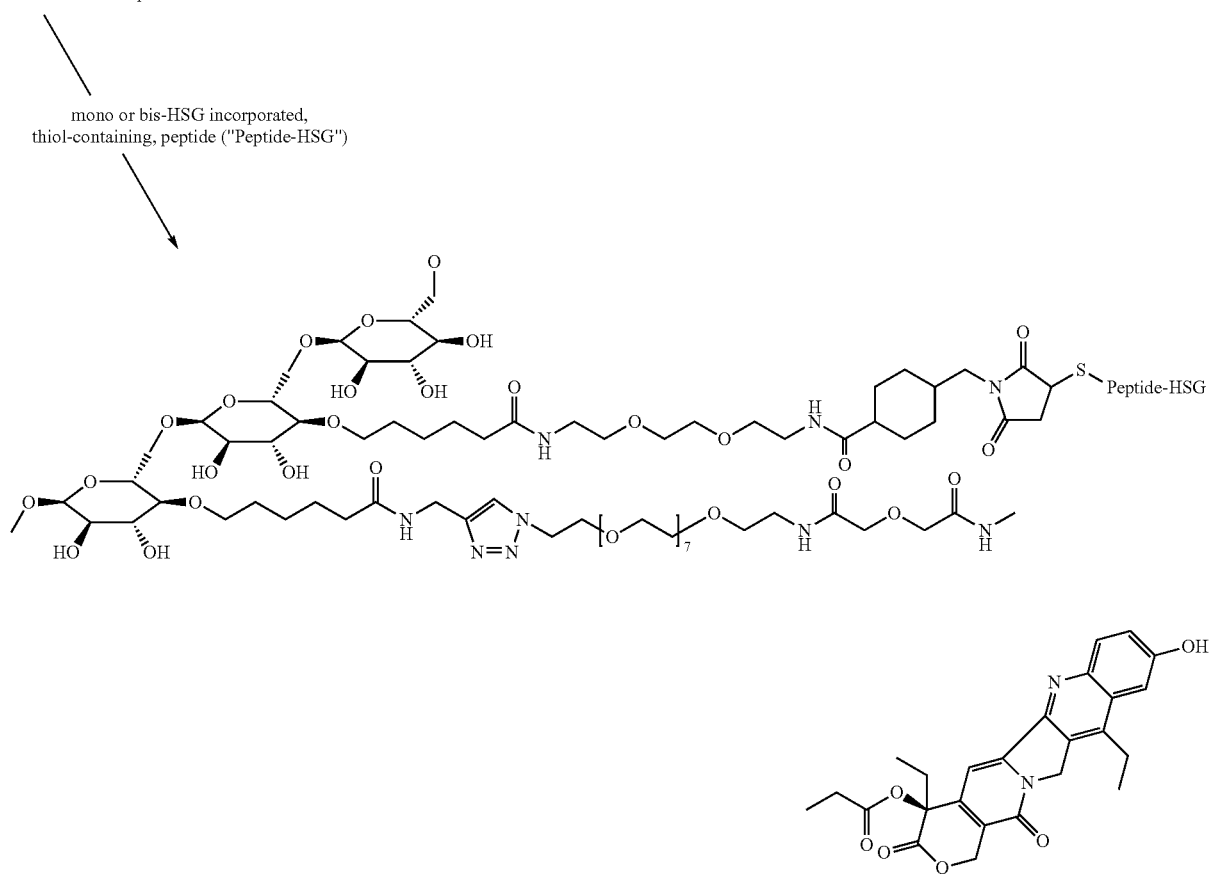

Example 12

Derivatizations of Polyglutamic Acid

Poly-L-glutamic acid (PG) is reacted with EDC and propargylamine. The product, acetylene-added PG is then purified by repeated ultrafiltration-diafiltration. The acetylene content is estimated by back-titration of the underivatized carboxylic acid groups. The acetylene-appended PG is sequentially derivatized with the maleimide-containing amino compound of Example 8 by EDC-mediated coupling to COOH groups of PG, followed by acetylene-azide coupling using azide-derivatized doxorubicin of Examples 3 or 4, or azide-derivatized SN-38 of Examples 5, 6, or 7. The respective product is purified by ultrafiltration-diafiltration. When the azide-drug is of Example 6 or 7, a further deprotection of BOC and MMT groups is also carried out with hydrochloric acid or trifluoroacetic acid, as described in paragraph 0084. Finally, the material is derivatized with a thiol-containing recognition-moiety, as described in Example 11. PGs with molecular weights in the ranges of 750-5000, 3000-15,000, 15,000-50,000, and 50,000-100,000 are used in this context.

What is claimed is:

1. A method of preparing a modified dendrimer comprising:
   (a) obtaining a dendrimer molecule comprising surface carboxylic acid groups;
   (b) reacting one or more of the carboxylic acid groups with a carbodiimide and (i) an amine-containing acetylene molecule, or (ii) an amine-containing azide molecule to form an acetylene-derivatized or azide-derivatized dendrimer molecule;
   (c) reacting other carboxylic acid groups of the acetylene-derivatized or azide-derivatized dendrimer molecule with a carbodiimide and a maleimido amine to form a maleimide-appended, acetylene- or azide-derivatized dendrimer molecule;
   (d) reacting (i) the maleimide-appended, acetylene-derivatized dendrimer molecule with an azide-derivatized drug or (ii) the maleimide-appended, azide-derivatized dendrimer molecule with an acetylene-derivatized drug to form a maleimide-appended, drug modified dendrimer molecule; and
   (e) forming a covalent bond between the maleimide-appended, drug modified dendrimer molecule and a thiol-containing compound comprising a recognition moiety to form a recognition moiety-appended, drug-modified dendrimer molecule, wherein the recognition moiety is selected from the group consisting of (i) somatostatin, (ii) folic acid, (iii) biotin, (iv) an antibody that binds to a hapten HSG or In-DTPA and (v) an antibody or antigen binding fragment thereof wherein the antibody is hR1 (anti-IGFR), RS7 (anti-EGP-1), LL1 (anti-CD74), LL2 (anti-CD22), RFB4 (anti-CD22), A20 (anti-CD20), A19 (anti-CD19), IMMU31 (anti-AFP), PAM4 (anti-MUC-1), KC4 (anti-MUC-1), MN-3 (anti-CEA), MN-14 (anti-CEA), MN-15 (anti-CEA), Mu-9 (anti-colon-specific antigen-p), Immun 31 (anti-alpha-fetoprotein), CC49 (anti-TAG-72), J591 (anti-prostate specific membrane antigen), G250 (anti-carbonic anhydrase IX) and L243 (anti-HLA-DR).

2. The method of claim 1, wherein the drug is attached to the dendrimer by a click chemistry reaction.

3. The method of claim 1, wherein the dendrimer is attached to two or more different drugs.

4. The method of claim 3, wherein the two different drugs are SN-38 and doxorubicin.

5. The method of claim 1, wherein the drug is attached to the dendrimer with a cleavable linker.

6. The method of claim 1, wherein the dendrimer is attached to 1 to 10 recognition moieties.

7. The method of claim 6, wherein the dendrimer is attached to 1 to 2 recognition moieties.

8. The method of claim 6, wherein the dendrimer is attached to 1 recognition moiety.

9. The method of claim 1, wherein the dendrimer is derivatized with an amine-containing acetylene molecule in step (b), and step (d) involves an azide-derivatized drug.

10. The method of claim 1, wherein the dendrimer is derivatized with amine-containing azide molecule in step (b), and step (d) involves an acetylene-derivatized drug.

11. The method of claim 1, wherein the drug is selected from the group consisting of a chemotherapeutic drug, vinca alkaloid, anthracycline, epipodophyllotoxin, taxane, antimetabolite, alkylating agent, antibiotic, Cox-2 inhibitor, antimitotic agent, antiangiogenic agent, pro-apoptotic agent, doxorubicin, methotrexate, paclitaxel, camptothecin, nitrogen mustards, alkyl sulfonate, nitrosourea, triazene, folic acid analog, pyrimidine analog, purine analog, platinum coordination complex, hormone, toxin, ricin, abrin, ribonuclease (RNase), DNase I, Staphylococcal enterotoxin-A, pokeweed antiviral protein, gelonin, diphtheria toxin, Pseudomonas exotoxin and Pseudomonas endotoxin.

12. The method of claim 1, wherein the drug is selected from the group consisting of 5-fluorouracil, aplidin, azaribine, anastrozole, anthracycline, bendamustine, bleomycin, bortezomib, bryostatin-1, busulfan, calicheamicin, camptothecin, carboplatin, 10-hydroxycamptothecin, carmustine, celecoxib, chlorambucil, cisplatinum, Cox-2 inhibitor, irinotecan (CPT-11), SN-38, carboplatin, cladribine, camptothecan, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agent, etoposide (VP16), etoposide glucuronide, etoposide phosphate, floxuridine (FUdR), 3', 5'-O-dioleoyl-FudR (FUdR-dO), fludarabine, flutamide, farnesyl-protein transferase inhibitor, gemcitabine, hydroxyurea, idarubicin, ifosfamide, L-asparaginase, lenalidomide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicamycin, procarbazine, paclitaxel, pentostatin, PSI-341, raloxifene, semustine, streptozocin, tamoxifen, temazolomide, trans-platinum, thalidomide, thioguanine, thiotepa, teniposide, topotecan, uracil mustard, vinorelbine, vinblastine, vincristine and vinca alkaloid.

13. The method of claim 1, wherein the drug is doxorubicin or SN-38.

14. The method of claim 5, wherein the cleavable linker comprises a hydrazone, a cathepsin-B-cleavable peptide, a disulfide or an ester bond.

15. The method of claim 1, wherein the drug is selected from the group consisting of SN-38-20-O-glycinato-PEG-azide, N3-PEG-Phe-Lys(monomethoxytrityl)-PABOCO-20-O-SN-38-10-O-BOC and azido-PEG-Phe-Lys(monomethoxytrityl)-PABOCO-20-O-glycinato-SN-38,
wherein the method further comprises removing BOC and monomethoxytrityl protecting groups from the recognition moiety-appended, drug-modified dendrimer molecule.

* * * * *

SEQUENCE LISTING

<160> NUMBER OF SEQ ID NOS: 20

<210> SEQ ID NO 1
<211> LENGTH: 44
<212> TYPE: PRT
<213> ORGANISM: Homo sapiens

<400> SEQUENCE: 1

Ser His Ile Gln Ile Pro Pro Gly Leu Thr Glu Leu Leu Gln Gly Tyr
 1               5                  10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Cys Gly His Ile Gln Ile Pro Pro Gly Leu Thr Glu Leu Leu Gln Gly
 1               5                  10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ile Glu Tyr Leu Ala Lys Gln Ile Val Asp Asn Ala Ile Gln Gln
 1               5                  10                  15

Ala

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Gly Gln Ile Glu Tyr Leu Ala Lys Gln Ile Val Asp Asn Ala Ile
 1               5                  10                  15

Gln Gln Ala Gly Cys
            20

<210> SEQ ID NO 5
<211> LENGTH: 44
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: Any conservative amino acid substitution
<220> FEATURE:
<221> NAME/KEY: MOD_RES
<222> LOCATION: (4)..(4)
<223> OTHER INFORMATION: Any conservative amino acid substitution
<220> FEATURE:
<221> NAME/KEY: MOD_RES
<222> LOCATION: (6)..(8)
<223> OTHER INFORMATION: Any conservative amino acid substitution
<220> FEATURE:
<221> NAME/KEY: MOD_RES
<222> LOCATION: (10)..(11)
<223> OTHER INFORMATION: Any conservative amino acid substitution
<220> FEATURE:
<221> NAME/KEY: MOD_RES
<222> LOCATION: (14)..(15)
<223> OTHER INFORMATION: Any conservative amino acid substitution
<220> FEATURE:
<221> NAME/KEY: MOD_RES
<222> LOCATION: (17)..(17)
<223> OTHER INFORMATION: Any conservative amino acid substitution
<220> FEATURE:
<221> NAME/KEY: MOD_RES
<222> LOCATION: (19)..(19)
<223> OTHER INFORMATION: Any conservative amino acid substitution
<220> FEATURE:
<221> NAME/KEY: MOD_RES
<222> LOCATION: (22)..(27)
<223> OTHER INFORMATION: Any conservative amino acid substitution
<220> FEATURE:
<221> NAME/KEY: MOD_RES
<222> LOCATION: (30)..(30)
<223> OTHER INFORMATION: Any conservative amino acid substitution
<220> FEATURE:
<221> NAME/KEY: MOD_RES
<222> LOCATION: (32)..(32)
<223> OTHER INFORMATION: Any conservative amino acid substitution
<220> FEATURE:
<221> NAME/KEY: MOD_RES
<222> LOCATION: (34)..(34)
<223> OTHER INFORMATION: Any conservative amino acid substitution
<220> FEATURE:
<221> NAME/KEY: MOD_RES
<222> LOCATION: (37)..(38)
<223> OTHER INFORMATION: Any conservative amino acid substitution
<220> FEATURE:
<221> NAME/KEY: MOD_RES
<222> LOCATION: (40)..(44)
<223> OTHER INFORMATION: Any conservative amino acid substitution

<400> SEQUENCE: 5

Xaa Xaa Ile Xaa Ile Xaa Xaa Xaa Leu Xaa Xaa Leu Leu Xaa Xaa Tyr
1               5                   10                  15

Xaa Val Xaa Val Leu Xaa Xaa Xaa Xaa Xaa Xaa Leu Val Xaa Phe Xaa
            20                  25                  30

Val Xaa Tyr Phe Xaa Xaa Leu Xaa Xaa Xaa Xaa Xaa
        35                  40

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any conservative amino acid substitution
<220> FEATURE:
<221> NAME/KEY: MOD_RES
```

```
<222> LOCATION: (7)..(8)
<223> OTHER INFORMATION: Any conservative amino acid substitution
<220> FEATURE:
<221> NAME/KEY: MOD_RES
<222> LOCATION: (11)..(12)
<223> OTHER INFORMATION: Any conservative amino acid substitution
<220> FEATURE:
<221> NAME/KEY: MOD_RES
<222> LOCATION: (15)..(17)
<223> OTHER INFORMATION: Any conservative amino acid substitution

<400> SEQUENCE: 6

Xaa Xaa Xaa Xaa Xaa Ala Xaa Xaa Ile Val Xaa Xaa Ala Ile Xaa Xaa
1               5                   10                  15

Xaa

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Ile Glu Tyr Val Ala Lys Gln Ile Val Asp Tyr Ala Ile His Gln
1               5                   10                  15

Ala

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Ile Glu Tyr Lys Ala Lys Gln Ile Val Asp His Ala Ile His Gln
1               5                   10                  15

Ala

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ile Glu Tyr His Ala Lys Gln Ile Val Asp His Ala Ile His Gln
1               5                   10                  15

Ala

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ile Glu Tyr Val Ala Lys Gln Ile Val Asp His Ala Ile His Gln
1               5                   10                  15
```

Ala

<210> SEQ ID NO 11
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Glu Gln Tyr Ala Asn Gln Leu Ala Asp Gln Ile Ile Lys Glu Ala
1               5                   10                  15

Thr Glu

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Phe Glu Glu Leu Ala Trp Lys Ile Ala Lys Met Ile Trp Ser Asp Val
1               5                   10                  15

Phe Gln Gln Cys
            20

<210> SEQ ID NO 14
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 15
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 17
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any conservative amino acid substitution
<220> FEATURE:
<221> NAME/KEY: MOD_RES
<222> LOCATION: (4)..(4)
<223> OTHER INFORMATION: Any conservative amino acid substitution
<220> FEATURE:
<221> NAME/KEY: MOD_RES
<222> LOCATION: (7)..(7)
<223> OTHER INFORMATION: Any conservative amino acid substitution
<220> FEATURE:
<221> NAME/KEY: MOD_RES
<222> LOCATION: (10)..(10)
<223> OTHER INFORMATION: Any conservative amino acid substitution
<220> FEATURE:
<221> NAME/KEY: MOD_RES
<222> LOCATION: (18)..(18)
<223> OTHER INFORMATION: Any conservative amino acid substitution
<220> FEATURE:
<221> NAME/KEY: MOD_RES
<222> LOCATION: (23)..(23)
<223> OTHER INFORMATION: Any conservative amino acid substitution
<220> FEATURE:
<221> NAME/KEY: MOD_RES
<222> LOCATION: (26)..(26)
<223> OTHER INFORMATION: Any conservative amino acid substitution
<220> FEATURE:
<221> NAME/KEY: MOD_RES
<222> LOCATION: (33)..(34)
<223> OTHER INFORMATION: Any conservative amino acid substitution
<220> FEATURE:
<221> NAME/KEY: MOD_RES
<222> LOCATION: (37)..(38)
<223> OTHER INFORMATION: Any conservative amino acid substitution
<220> FEATURE:
<221> NAME/KEY: MOD_RES
<222> LOCATION: (40)..(40)
<223> OTHER INFORMATION: Any conservative amino acid substitution
<220> FEATURE:
<221> NAME/KEY: MOD_RES
<222> LOCATION: (42)..(42)
<223> OTHER INFORMATION: Any conservative amino acid substitution
<220> FEATURE:
<221> NAME/KEY: MOD_RES
<222> LOCATION: (44)..(44)
<223> OTHER INFORMATION: Any conservative amino acid substitution
```

```
-continued

<400> SEQUENCE: 17

Xaa His Ile Xaa Ile Pro Xaa Gly Leu Xaa Glu Leu Leu Gln Gly Tyr
1               5                   10                  15

Thr Xaa Glu Val Leu Arg Xaa Gln Pro Xaa Asp Leu Val Glu Phe Ala
            20                  25                  30

Xaa Xaa Tyr Phe Xaa Xaa Leu Xaa Glu Xaa Arg Xaa
        35                  40

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Lys Ser Leu Ser Leu Ser Pro Gly Leu Gly Ser Gly Gly Gly Gly
1               5                   10                  15

Ser Gly Gly Cys Gly
            20

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Lys Ser Leu Ser Leu Ser Pro Gly Ala Gly Ser Gly Gly Gly Gly
1               5                   10                  15

Ser Gly Gly Cys Gly
            20

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Lys Ser Leu Ser Leu Ser Pro Gly Gly Ser Gly Gly Gly Gly Ser
1               5                   10                  15

Gly Gly Cys Gly
        20
```